United States Patent
Eyal et al.

(10) Patent No.: US 6,320,077 B1
(45) Date of Patent: *Nov. 20, 2001

(54) LACTIC ACID PROCESSING; METHODS; ARRANGEMENTS; AND, PRODUCT

(75) Inventors: Aharon M. Eyal, Jerusalem (IL); John N. Starr, Chaska; Rod Fisher, Eden Prairie, both of MN (US); Betty Hazan, Jerusalem; Riki Canari, Beit Zeit, both of (IL); David R. Witzke, Oskaloosa, IA (US); Patrick R. Gruber, Blaine; Jeffrey J. Kolstad, Wayzata, both of MN (US)

(73) Assignee: Cargill, Incorporated, Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/132,720

(22) Filed: Aug. 12, 1998

Related U.S. Application Data

(63) Continuation of application No. 08/950,289, filed on Oct. 14, 1997, application No. 09/284,160, filed on Oct. 25, 1999.

(51) Int. Cl.$^7$ .......................... C07C 59/08; C07C 51/42; C12P 7/56

(52) U.S. Cl. .................... 562/589; 562/580; 562/593; 435/139

(58) Field of Search ...................... 562/589, 580; 562/593; 435/139

(56) References Cited

U.S. PATENT DOCUMENTS

| | | |
|---|---|---|
| 1,906,068 | 4/1933 | Jenemann . |
| 2,223,797 | 12/1940 | Tindall . |
| 2,261,926 | 11/1941 | Nolte et al. . |
| 2,331,948 | 10/1943 | Ward et al. . |
| 2,350,370 | 6/1944 | Schopmeyer et al. . |
| 2,415,558 | 2/1947 | Hesler et al. . |
| 2,539,472 | 1/1951 | Ratchford et al. . |
| 2,710,880 | 6/1955 | Filachione et al. . |
| 4,142,023 | 2/1979 | Bornstein et al. . |
| 4,275,234 | 6/1981 | Baniel et al. . |
| 4,282,323 | 8/1981 | Yates . |
| 4,334,095 | 6/1982 | Baniel . |
| 4,405,717 | 9/1983 | Urbas . |
| 4,444,881 | 4/1984 | Urbas . |
| 4,467,034 | 8/1984 | Voelskow et al. . |
| 4,698,303 | 10/1987 | Bailey et al. . |
| 4,769,329 | 9/1988 | Cooper et al. . |
| 4,771,001 | 9/1988 | Bailey et al. . |
| 5,068,418 | 11/1991 | Kulprathipanja et al. . |
| 5,068,419 | 11/1991 | Kulprathipanja et al. . |
| 5,071,754 | 12/1991 | Walkup et al. . |
| 5,132,456 | 7/1992 | King et al. . |
| 5,138,074 | 8/1992 | Bellis et al. . |
| 5,142,023 | 8/1992 | Gruber et al. . |
| 5,210,296 | * 5/1993 | Cockrem et al. .................... 562/589 |

(List continued on next page.)

FOREIGN PATENT DOCUMENTS

| | | |
|---|---|---|
| 1 049 846 | 2/1959 | (DE) . |
| 0 076 123 | 4/1983 | (EP) . |
| 0 216 221 A1 | 4/1987 | (EP) . |
| 0 308 064 | 3/1989 | (EP) . |
| 0 517 242 A2 | 12/1992 | (EP) . |
| 0 614 983 | 9/1994 | (EP) . |
| 907321 | 10/1962 | (GB) . |
| 2 251 864 | 7/1992 | (GB) . |
| 33552 | 7/1969 | (IL) . |
| WO 85/01064 | 3/1985 | (WO) . |

(List continued on next page.)

OTHER PUBLICATIONS

Chen et al, Appl. Biochem. biotechnol. (1997), 63–65, 435–448, Apr. 1997.*

Rixey, W. et al., "Fixed–Bed Mulisolute Adsorption Characteristics of Nonwet Adsorbents", *AIChE Journal*, vol. 35, No. 1, pp. 69–74 (Jan. 1989).

Rixey, W. et al., "Wetting and Adsorption Properties of Hydrophobic Macroreticular Polymeric Adsorbents", *Journal of Colloid and Interface Science*, vol. 131, No. 2, pp. 320–332 (Sep. 1989).

Nakamura, L.K. et al., 1977, *Developments in Industrial Microbiology*, Proceedings of the Thirty–Fourth General Meeting of the Society for Industrial Microbiology Held at East Lansing, MI, Aug. 21–26, 1977 "Microbiology of Corn Fermented with Swine Waste".

Roy, T.B.V. et al., 1982, *Biotechnology Letters*, 4(8):483–488 "Lactic Acid Production by *Lactobacillus Delbreuckii* in a Hollow Fiber Fermenter".

Roy, T.B.V. et al., 1983, *Biotechnology Letters*, 5(10):665–670 "The Application of Cell Recycle to Continuous Fermentative Lactic Acid Production".

Stenroos, S.L. et al., 1982, *Biotechnology Letters*, 4(3):159–164 "Production of L.–Lactic Acid with Immobilized *Lactobacillus Delbrueckii*".

(List continued on next page.)

Primary Examiner—Sreeni Padmanabhan
(74) *Attorney, Agent, or Firm*—Merchant & Gould P.C.

(57) ABSTRACT

The techniques for processing lactic acid/lactate salt mixtures are provided. Preferred mixtures for processing are obtained from fermentation broths, preferably from fermentation processes conducted at a pH of 4.8 or lower. The techniques generally concern the provision of separated lactic acid and lactate streams, from the mixtures. Preferred techniques of separation and processing of each of the streams are provided.

20 Claims, 11 Drawing Sheets

U.S. PATENT DOCUMENTS

| | | |
|---|---|---|
| 5,247,058 | 9/1993 | Gruber et al. . |
| 5,247,059 | 9/1993 | Gruber et al. . |
| 5,258,488 | 11/1993 | Gruber et al. . |
| 5,274,073 | 12/1993 | Gruber et al. . |
| 5,338,822 | 8/1994 | Gruber et al. . |
| 5,349,084 | 9/1994 | Shishikura et al. . |
| 5,357,034 | 10/1994 | Fridman et al. . |
| 5,357,035 | 10/1994 | Gruber et al. . |
| 5,359,026 | 10/1994 | Gruber . |
| 5,420,304 | 5/1995 | Verser et al. . |
| 5,446,123 | 8/1995 | Gruber et al. . |
| 5,475,080 | 12/1995 | Gruber et al. . |
| 5,484,881 | 1/1996 | Gruber et al. . |
| 5,510,526 | 4/1996 | Baniel et al. . |
| 5,521,278 | 5/1996 | O'Brien et al. . |
| 5,525,706 | 6/1996 | Gruber et al. . |
| 5,536,807 | 7/1996 | Gruber et al. . |
| 5,539,081 | 7/1996 | Gruber et al. . |
| 5,585,191 | 12/1996 | Gruber et al. . |
| 5,594,095 | 1/1997 | Gruber et al. . |
| 5,641,406 | 6/1997 | Sarhaddar et al. . |
| 5,681,728 | 10/1997 | Miao et al. ............................ 435/136 |
| 5,746,920 | 5/1998 | Boergardes et al. . |
| 5,766,439 | 6/1998 | Eyal et al. . |
| 5,773,653 | 6/1998 | Baniel . |
| 5,780,276 | 7/1998 | Baniel . |
| 5,786,185 | 7/1998 | Tsao et al. . |
| 5,831,122 | 11/1998 | Eyal . |

FOREIGN PATENT DOCUMENTS

| | | |
|---|---|---|
| WO 93/00440 | 1/1993 | (WO) . |
| WO 93/06226 | 4/1993 | (WO) . |
| WO 95/03268 | 2/1995 | (WO) . |
| WO 95/25081 | 9/1995 | (WO) . |
| WO 95/32301 | 11/1995 | (WO) . |
| WO 9711047 A1 | 3/1997 | (WO) . |
| WO 97/35489 | 10/1997 | (WO) . |
| WO 98/15517 | 4/1998 | (WO) . |
| WO 98/15519 | 4/1998 | (WO) . |

OTHER PUBLICATIONS

Stieber, R.W. et al., 1981, *Biotechnology and Bioengineering*, XXIII(2):534–549 "Dialysis Continuous Process for Ammonium Lactate Fermentation: Simulated and Experimental Dialysate–Feed, Immobilized–Cell Systems".

Cann, I., et al., "Characterization of Two Novel Saccharolytic Aerotolerant Thermophiles, *Thermobacter polysaccarolyticum* gen. nov., sp. nov. and *Thermobacter zeae* gen. nov., sp. nov.", Department of Animal Sciences, University of Illinois at Urbana–Champaign, Urbana, IL 61801; 20 pages (undated).

Mehaia, M., et al., "Lactic Acid Whey Permeate in Membrane Recycle Bioreactor", *Enzyme Microb. Technol.*, 8:289–292 (May 1986).

Fukunishi, Kunio, Chemical Abstracts, vol. 107, No. 1, 1987 "Production of optically active lactic acid" p. 543.

Nakahara, Tadaatsu, et al., Chemical Abstracts, vol. 118, No. 5, 1993 "Manufacture of D–lactic acid from 1,2–propanediol with Pseudomonas", p. 559.

San–Martin, M. et al., "Liquid–Liquid Extraction of Lactic Acid with Alamine 336", *Journal of Chemical Technology and Biotechnology*, vol. 65, No. 3; Mar. 1, 1996; pp. 281–285.

Peters, E., "Microbiological and Biochemical Characterization of the Steeping Phase of the Corn Wet Milling Process" (abstract of a thesis submitted in partial fulfillment of requirements for degree), University of Iowa, pp. i–v, 39–57, 62–64, 77–79, 83–100, 105–007, 115 (May 1996).

Yabannavar, V., et al., "Extractive Fermentation for Lactic Acid Production", *Biotechnology and Bioengineering*, 37:1095–1100 (1991).

Grimont, F., et al., "Ribosomal Ribonucleic Acid Gene Restriction Patterns as Potential Taxonomic Tools," *Ann. Inst. Pasteur/Microbiol.* (Paris), 1378:165–175, (1986).

Jacquet, et al., "Typing of Listeria monocytogenes by Restriction Polymorphism of the Ribosomal Ribonucleic Acid Gene Region," *Zbl. Bakt.*, 276:356–365, (1992).

Stanbury, P., et al., "Principles of Fermentation Technology," 1984, Pergamon Press, pp. 33–37.

Blumberg et al., 1974, *Proceedings of the International Solvent Extraction Conference*, vol. 3, pp. 2789–2802 "Interesting Aspects in the Developement of a Novel Solvent Extraction Process for Producing Sodium Bicoarbonate".

Ricker et al., 1980, *J. Separ. Proc. Technol.* 1(2), pp. 23–30 "Solvent Extraction with Amines for Recovery of Acetic Acid from Dilute Aqueous Industrial Streams".

Cheng et al., 1991, *Journal of Industrial Microbiology*, vol. 7, pp. 27–34 "Lactic Acid Production From Enzyme–Thinned Corn Starch Using *Lactobacillus Amylovorus*".

Davison et al., 1992, *Biotechnology and Bioengineering*, vol. 39, pp. 365–368 "A Proposed Biparticle Fluidized–Bed for Lactic Acid Fermentation and Simultaneous Adsorption".

Benthin et al., 1995, *Appl Microbiol Biotechnol*, vol. 42, pp. 826–829 "Production of Optically Pure D–Lactate by *Lactobacillus Bulgaricus* and Purification by Crystallisation and Liquid/Liquid Extraction".

Gonzalez–Vara et al., 1996, *Journal of Fermentation and Bioengineering*, vol. 81, No. 6, pp. 548–552 "Production of L(+) and D(–) Lactic Acid Isomers by *Lactobacillus casei* subsp. casei DSM 20011 and *Lactobacillus coryniformis* subsp. torquens DSM 20004 in Continuous Fermentation".

Ye et al., 1996, *Journal of Fermentation and Bioengineering*, vol. 81, No. 3, pp. 240–246 "Performance Improvement of Lactic Acid Fermentation by Multistage Extractive Fermentation".

\* cited by examiner

LACTIC ACID PROCESSING; METHODS; ARRANGEMENTS; AND, PRODUCT

This application is a Continuation application Ser. No. 08/950,289, filed Oct. 14, 1997, which application are incorporated herein by reference.

FIELD OF THE INVENTION

The present invention relates to lactic acid processing. It particularly concerns: methods for separating lactic acid streams and lactate salt streams from mixtures such as fermentation broths; isolating and processing the lactic acid; and, isolating the lactate salt in preferred forms.

BACKGROUND OF THE INVENTION

The potential of lactic acid as a commodity chemical, for example for use in the production of various industrial polymers, is known. This has been described, for example, in U.S. Pat. Nos.: 5,142,023; 5,247,058; 5,258,488; 5,357,035; 5,338,822; 5,446,123; 5,539,081; 5,525,706; 5,475,080; 5,359,026; 5,484,881; 5,585,191; 5,536,807; 5,247,059; 5,274,073; 5,510,526; and 5,594,095. (The complete disclosures of these seventeen patents, which are owned by the assignee of the present application, Cargill, Inc. of Minneapolis, Minn., are incorporated herein by reference.) There has been general interest in developing improved techniques for generation and isolation of lactic acid. Also, because of their potential commercial value, there is great interest in isolation of the other valuable related lactate products such as lactide, lactate esters and amides, and oligomers; see e.g. the same 17 patents.

In general, large amounts of lactic acid can be readily generated by the conduct of large-scale, industrial, bacterially-conducted fermentation processes, particularly using carbohydrates, such as dextrose, as the feed stock, along with suitable mineral and amino acid based nutrients. Typically, such productions occur at broth temperatures of at least 45° C., usually around 48° C.

Issues of concern with respect to lactic acid generation include, inter alia, appropriate control of pH within the fermentation system to ensure proper environment for bacterial action; separation and isolation of either or both of lactic acid and lactate salts from the fermentation process; and downstream isolation and production involving the isolated lactic acid or lactic acid derived product.

SUMMARY OF THE INVENTION

According to the present disclosure, techniques for processing mixtures of lactic acid and dissolved lactate salts are provided. The preferred techniques are provided for processing fermentation broths, preferably fermentation broths produced with or adjusted to have a pH of less than about 4.8, typically and preferably less than about 4.5, more preferably less than 4.3 and most preferably within the range of about 3.0 to 4.2 inclusive.

The techniques concern processing the mixtures into: (a) a lactic acid stream, component or phase; and, (b) a lactate salt stream component or phase. Preferred techniques are provided so that the lactic acid stream, component or phase can be readily taken on to produce desirable lactate products, such as lactate oligomers, lactide lactate esters, lactate amides and/or polylactate. The preferred processing also provides the lactate salt in a form suitable for further use, such as recycling to a fermentation broth; or, for as a fertilizer or feed.

DETAILED DESCRIPTION

Figure 1:
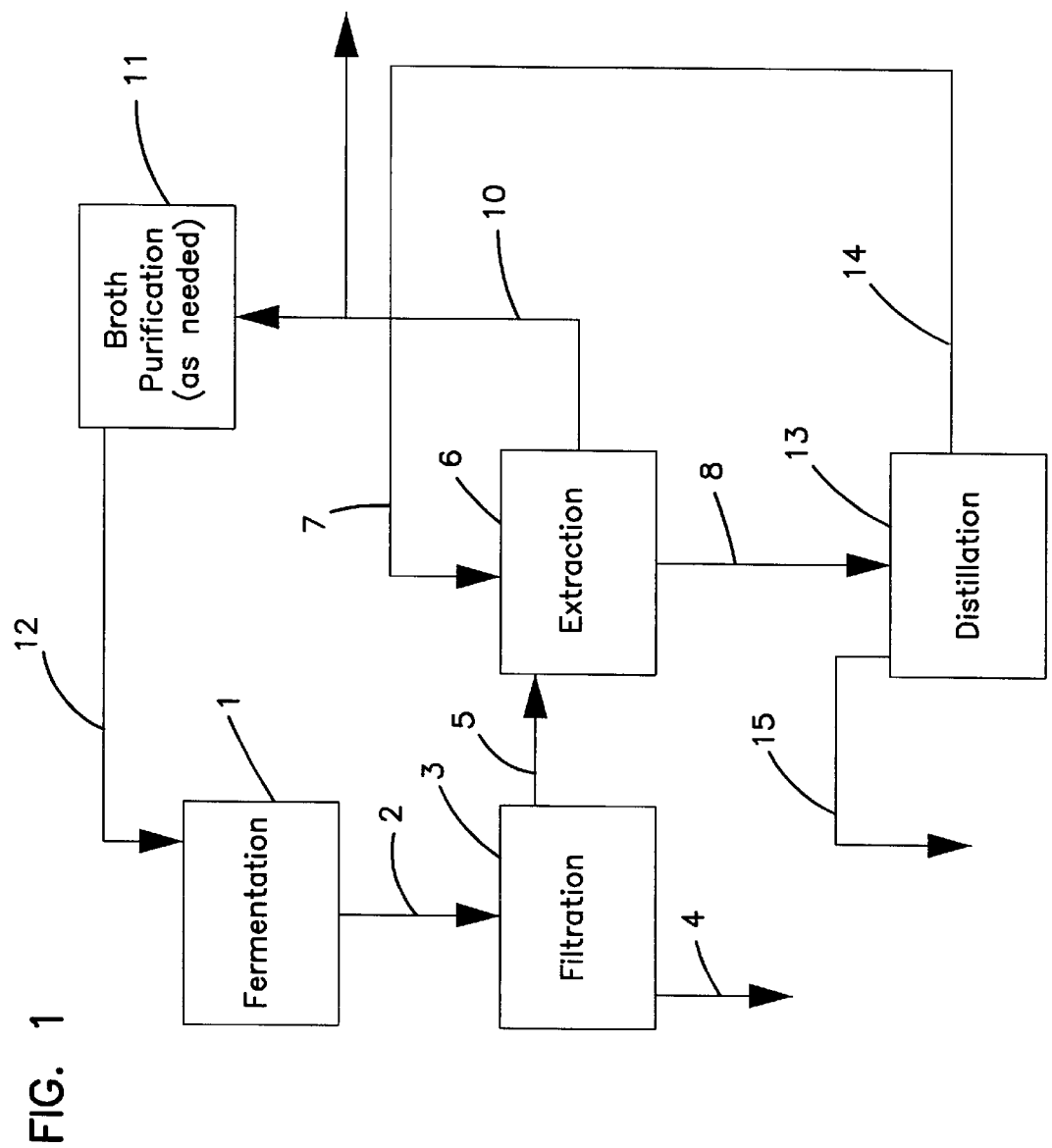
FIG. 1 is a process flow chart of a process according to the present disclosure.

I. Selected Issues of Concern with Respect to Lactic Acid Processing, Isolation and Use

A. Chirality

Lactic acid has a chiral center and is found in both the D and L forms. The chiral purity of the lactic acid is important with respect to meeting the needs of industrial applications, see for example U.S. Pat. Nos.: 5,142,023; 5,338,822; 5,484,881; and 5,536,807. There are bacteria, for example from the Lactobacillus genus, that can make either the D-lactic acid or the L-lactic acid. However, it is typical that any one bacteria strain makes a vast majority of only one enantiomer. Indeed, fermentation broths with high chiral purity (90% or greater) of lactic acid can be readily obtained. This chirality is obtained from the metabolism of dextrose or other carbohydrates by microorganism cells during fermentation. For example, *Lactobacillus bulgaricas* and *Lactobacillus coryniformis* typically make the D-lactic acid enantiomer almost exclusively. *Lactobacillus casei* has been found to produce, in majority, L-lactic acid.

For polylactic acid applications, the chiral purity of the lactic acid has a strong influence on the properties of the polymer. The chiral purity of the polymer controls the ability of the polymer to crystallize; See for example U.S. Pat. Nos.: 5,484,881; 5,585,191; and, 5,536,807; and, commonly assigned U.S. patent application Ser. No. 08/850,319 filed May 2, 1997. (Each of these four references is incorporated herein by reference.) In some instances, polymers with controlled amounts of crystallinity are desired in order to get polymer properties that are advantageous in an industrial application, for example to raise the heat distortion temperature of the polymer. Other advantages of controlled polymer crystallinity relate to the storage, transfer and processing of polylactic acid resins into fibers, non-woven fabrics, films, and other end products.

Lactic acid currently used in food applications has chiral purity requirements greater than 95% chiral purity, generally with a preference for the "L" form. The chiral purity of lactic acid is also important for end products such as pharmaceuticals and other medical devices where lactic acid is a starting material. Herein the term "95% chiral purity" means 95% of the lactic acid/lactate content is one the of two possible enantiomers. (Thus, the composition could alternatively be characterized as 10% racemic or 90% optically pure.)

Herein the terms "polylactic acid" or "polylactate" are intended to refer to any polymer comprising at least 50% by wt. polymer units of lactic acid residue or lactide residue. Thus, the two terms include within their scope polylactides. The terms "polylactic acid" and "polylactate" are not meant to specifically identify the polymerized monomer, for example whether the material polymerized was lactide (lactic acid dimer) or lactic acid itself

B. Control of pH During Fermentation

Most microorganisms have a range of pH in which they are able to most efficiently carry out metabolism. Therefore, the pH of the fermentation is a processing variable that strongly affects the overall productivity of the microorganism cells in the fermentation.

The Lactobacillus microorganisms produce lactic acid. Without a neutralizing agent, the pH of a typical, conventional, fermentation broth quickly drops to a value at which most of the microorganisms die or cease useful production. Therefore, addition of a neutralizing agent has typically been required to meet the economic need for a fermentation with high overall productivity. The pH value for many lactic acid fermentations with good productivity (i.e. >0.5 g lactic material (lactic acid and lactate salt) produced/liter/hr) are in the range of 5.0 to 7.0; see, for example, U.S. Pat. No. 5,510,526. Much work has been done to look for organisms that retain high lactic acid productivities while operating in broths at pH ranges from about 3.0 to 4.8. This is discussed below.

Lactic acid (HLa or LaH) dissociates into a proton, $H^+$, and a lactate anion, $La^{31}$ (sometimes referred to herein as dissolved lactate salt when another source of cation is present, typically from the buffering salt). The amount of dissociation is related to the pH of the solution and the $pK_a$ of lactic acid. The $pK_a$ of lactic acid at 25° C. is 3.86 (at 50° C. it is about 3.89). Equation 1 below describes how the pH, $pK_a$, and degree of lactic acid dissociation are related.

$$pH = pK_a + \log\frac{[La^-]}{[HLa]}.$$ Equation 1

Figure 11:
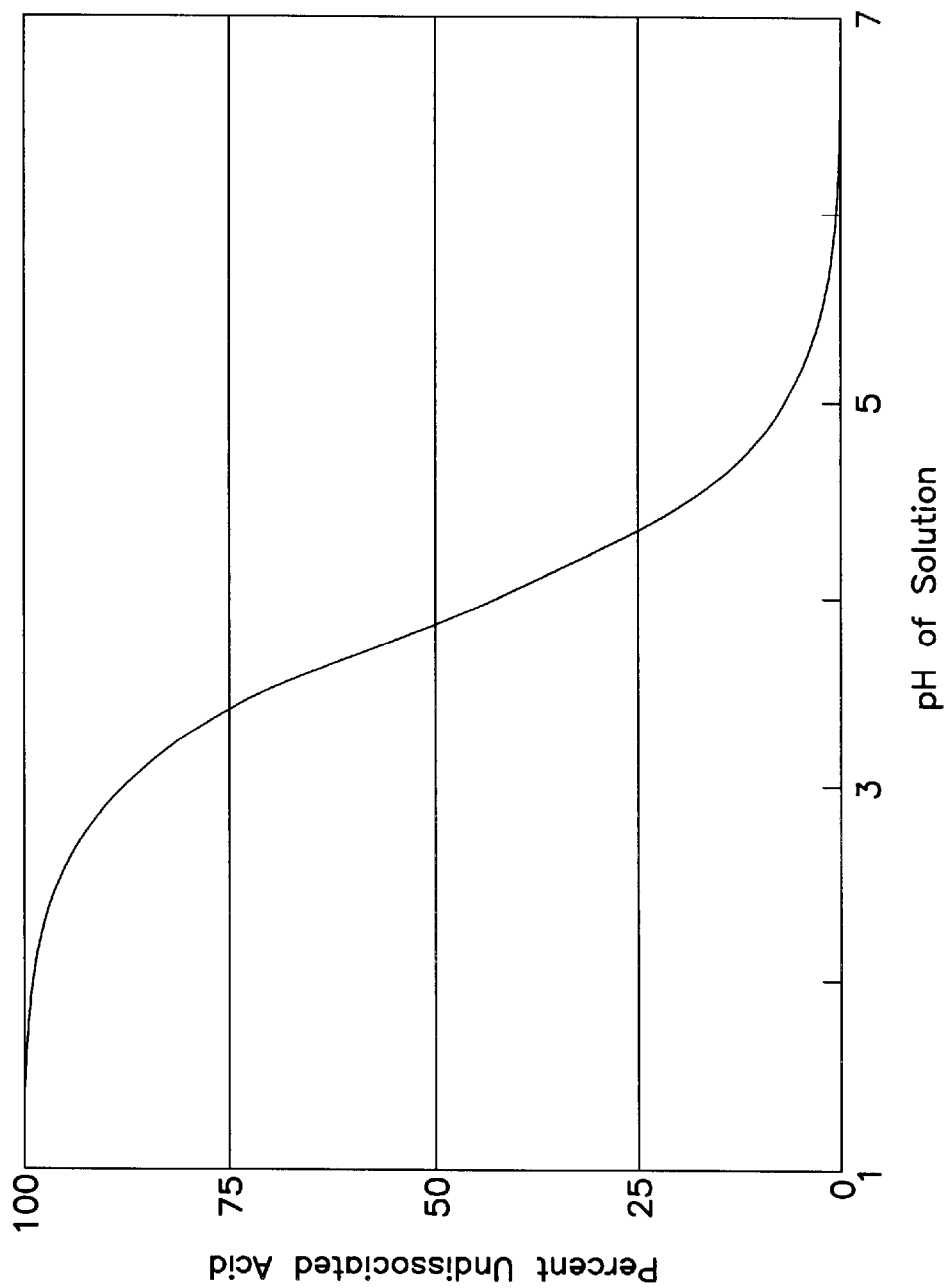
FIG. 11 is a graph showing percent of lactic acid in free acid form, in a lactic acid mixture, as a function of pH.

Equation 1 shows that half the acid is dissociated when the pH equals the $pK_a$ of the acid. At higher pH values, the majority of the lactic acid is in the lactate anion form. FIG. 11 is a graph which shows the percent of lactic acid in the undissociated (free acid) form as the pH varies from 1 to 7. The graph shows that the percent of undissociated lactic acid present in solution at the pH values of 5 to 7 is relatively low.

If the fermentation broth has a pH value between 3.0 and 4.5, there will be a significant amount of lactic acid in the undissociated form, see FIG. 11. Indeed at a pH of 3.0 the molar ratio of free lactic acid (undissociated) to lactate ion at 25° C. is about 7.0; and, at a pH of about 4.5 the ratio at 25° C., is about 0.23. A separation process that specifically separates the undissociated lactic acid or a lactate derivative and the lactate salt would be beneficial because it would provide a stream of: (1) lactic acid products to be further purified (and/or converted to lactide or polymer); and, (2) a lactate salt, useful as a buffering agent for pH control in the fermentor.

Equation 1 shows how the ratio of lactate anion, $La^-$, to free lactic acid HLa, is related to the pH of the solution. As free lactic acid is produced by the microorganism during fermentation, the addition of lactate salt can keep the pH of the solution constant. If the added lactate salt, for pH control, is a recycled material, then it follows that efficiency of conversion and recovery of raw material into lactic acid, in the overall fermentation processes, is improved. That is, a higher percentage of added feed stock is converted into, and is retained and isolated as, lactic acid, as opposed to lactate salt, due to the maintenance of the equilibria suggested by Equation 1 with recycling of lactate salt.

The preferred separation scheme to be employed will depend on the form of the lactate material in solution. The isolation of lactate material from an aqueous solution can require substantial energy, especially if the aqueous solution is at a pH greater than 4.5 and the lactate material is mainly present as a lactate salt, as opposed to an aqueous solution at a pH below 4.5 where a significant amount of lactate material is in the free acid form. When the pH of the fermentation broth is about 5 to 7, a typical step in conventional separation processes has been to strongly acidify the solution by the addition of sulfuric acid. This process forms the free lactic acid, but also forms a by-product salt (typically calcium sulfate). The formation of by-product salt represents the use of chemical energy to transform the lactate salt into lactic acid, and can create a waste disposal issue when manufacturing lactic acid on a large scale. In many alternative separation processes in which direct acidification does not occur, energy would be used to split the lactate salt back into lactic acid and a base. Water-splitting electrodialysis is a good example of this type of separation process in which electrical energy is used to form an acid and a base from the salt and water.

It is noted that as the desired product (HLa) from the fermentation builds in concentration, the fermentation is often not only inhibited due to pH but also due to HLa concentration.

C. Downstream Processing; Definition of Materials

Once the lactic acid is separated from the lactate salt, the lactic acid can be used to form high molecular weight polylactic acid (typically average M.W. from 10,000 to about 300,000). Processes such as those described in: U.S. Pat. Nos. 5,338,822; 5,446,123; 5,539,081; 5,525,706; 5,475,080; 5,359,026; 5,484,881; 5,585,191; 5,536,807; 5,247,059; 5,274,073; and 5,594,095, are typically and preferably used. Such techniques generally include: (a) providing a lactide mixture (optionally with other reactants such as other monomers and/or epoxidized oils) with an appropriate catalyst and a sufficiently low water presence; (b) polymerizing the lactide mixture, generally by application of heat; and, (c) devolatilization of the polylactide to remove unreacted monomer and residual water. Stabilizing agents such as free radical scavengers, and catalyst deactivators may be used, to provide the final composition with preferred melt stability.

Chemical intermediates formed from lactic acid, such as lactide, alkyl lactate esters, alkyl lactate amides, and oligomers with an average molecular weight less than about 5,000, are typically used to form polylactide polymers, sometimes by first being reacted to form lactide when an intermediate other than lactide itself is involved. Thus, generation and/or isolation of these identified "building blocks" for polymers, from the LaH of a fermentation broth, is of great interest. The term "lactic acid products" as used herein is meant to include lactic acid, lactate salts, alkyl lactate esters, alkyl lactate amides, lactide, lactoyl lactate, lactic acid trimers and tetramers and lactic acid oligomers, typically with an average molecular weight of less than about 5,000. Of course, lactic acid is the smallest repeating unit (present as the acid residue from condensation polymerization) in polylactic acid. It is the most basic starting material for polylactic acid, and the other chemical intermediates such as lactide and lactic acid oligomers are typically made from lactic acid (or lactate salts).

Lactide is a cyclic ester comprising of two lactic acid molecules. That is, it is a dimer of lactic acid. Due to the chiral nature of the lactic acid, lactide may have one of three types of optical activity depending upon whether it comprises two D-lactic acid residues, two L-lactic acid residues, or an L-lactic acid residue and a D-lactic acid residue. These three dimers are designated D-lactide, L-lactide, and meso-lactide, respectively. Lactide is fully dehydrated lactic acid, and is commonly used in the manufacture of polylactic acid (or polylactide) using a ring-opening reaction to grow the polymer to high molecular weights. Lactide can also be a key starting material in the production of other industrially relevant chemicals.

Alkyl lactate esters and alkyl lactate amides are compounds that can be used as feedstocks for lactic acid oligomers, lactide, or polylactic acid. To make lactic acid oligomers with an ester on the terminal carboxylic acid end, alkyl lactate esters can be transesterified with the corresponding alcohol being obtained along with the oligomer. The simultaneous or sequential removal of the alcohol drives the reaction to the oligomer formation. Lactide can be made from esterified lactic acid oligomers. The alkyl lactate amides would have similar chemistry to the esters, but with an amine being obtained along with the oligomer. Lactide can be made from a lactic acid oligomer with an amide group on the terminal carboxylic acid end.

Forming the esters or amides from the lactic acid may also aid in the separation of the lactic acid derivative from impurities. After a purified alkyl lactate ester or alkyl lactate amide stream is obtained, the ester or amide can be hydrolyzed to obtain the lactic acid and the corresponding alcohol or amine. The lactic acid can be separated from this mixture, and the alcohol or amine recycled back to the ester or amide formation step. Of course, certain lactic esters and amides could be further purified if needed. Useful alkyl lactate esters include: methyl lactate, ethyl lactate, butyl lactate, octyl lactate, dodecyl lactate, 2-ethyl hexyl lactate, and the lactate of 1,4-butane diol. Indeed, alkyl lactates with 1–20 carbon atoms in the alcohol residue, both saturated and unsaturated, are potentially useful. With respect to lactate esters and their use, see for example U.S. Pat. No. 5,247,059.

Lactamide (the ammonia amide of lactic acid) is an industrially important lactic amide. It is used in hair care products.

Lactic acid oligomers having an average molecular weight of less than about 5,000 are useful in making lactide. Techniques usable are described in U.S. Pat. No. 5,142,023, incorporated by reference. Certain preferred modifications described herein concern directly forming lactide even in the presence of residual extractant, such as residual trialkylamine. A catalyst can be used to increase the rate of lactide formation from polylactic acid oligomers. Many suitable catalysts are known, such as metal oxides, metal dusts, and organic metal compounds, see for example U.S. Pat. Nos.: 5,142,023; 5,338,822; and 5,594,095. To drive the lactide formation, the lactide is, typically, simultaneously or sequentially removed from the lactic acid oligomer stream. One method for this removal is the addition of heat to vaporize a crude lactide stream from the oligomers. In addition to use as precursors to lactides, lactic acid oligomers are useful as antimicrobial agents and as controlled release acidulants for food and agricultural use. Of course the oligomer may be terminated or functionalized, in some instances, as the amide or ester.

II. Lower pH Fermentation

Generation of lactic acid solutions, via bacteriological systems, having pHs on the order of 5.0 or below, preferably 4.8 or below and typically 3.5 to 4.5, lead to a greater percentage of production of the lactate material, in the lactic acid form. This is described, for example, in commonly assigned (to Cargill, Inc. of Minnetonka, Minn.), co-filed, U.S. patent application entitled LOW pH LACTIC ACID FERMENTATION, identifying Ting Carlson and Eugene Max Peters, Jr. as inventors (hereinafter referred to as the Carlson et al application). The Carlson et al application was filed on the same date of the present application (Oct. 14, 1997) and is incorporated herein by reference.

Again, generation of relatively large amounts of product from the fermentation process in the form of lactic acid, rather than lactate salt, is advantageous since it can reduce the need for, or extent of, certain follow-up process steps of acidulation and/or "salt splitting." That is, if a larger amount of the material is generated as free lactic acid, a processing step of generating the lactic acid from the lactate, and the expenses and consequences associated therewith, are reduced or avoided. Even if some acidulation is conducted, substantially less acid addition would be involved than would be the case with a high pH system.

In general, it has been determined that with processes conducted to render fermentation broths (or other lactic acid/lactate salt mixtures) at pHs on the order of about 4.8 or lower (preferably 4.5 or lower, most preferably 4.3 or lower, typically 3.5 to 4.2), an overall efficient process can be developed, in which the lactic acid generated is used in polymer production, and recovered lactate salt is recycled into the fermentation system as a buffering agent, or differently put for pH control.

The process of Carlson et al allows the efficient production of lactate and, in particular, the efficient production of high concentrations of free lactic acid via incubation of an acid-tolerant homolactic bacteria in a suitable nutrient medium. By "homolactic" it is meant that the bacteria strain produces substantially only lactic acid as the fermentation product. The acid-tolerant homolactic bacteria is typically isolated from the corn steep water of a commercial corn milling facility. While different bacteria of this type may produce racemic lactate, or lactate predominantly in either the D- or L- isomeric form, the process of Carlson et al describes preferred fermentation using a homolactic bacteria which produces the L-lactate, most preferably in optically pure form.

The process of Carlson et al allows the efficient production of relatively high concentrations of free lactic acid. This efficiency may be expressed in a variety of manners. The concentration of free lactic acid in the fermentation broth serves as one measure of the overall productivity of the process. The process of Carlson et al typically produces a broth containing at least about 25 g/L, preferably at least about 30 g/L, and more preferably at least about 40 g/L free lactic acid.

Most typically and preferably, the lactate produced by the fermentation process is predominantly of one chiral form, either D-lactate or L-lactate. For preferred downstream processing, an optical purity of the lactic acid from the fermentation process of at least 50%, more preferably at least 75% and most preferably at least 90% up to optically pure is produced in the fermentation and used. For example, one embodiment of the process described in Carlson et al includes incubating an acid-tolerant homolactic bacteria in a nutrient medium to produce L-lactate having an optical purity of at least about 50% (That is, it has a chiral purity of at least about 75%.). The process of Carlson et al can even be applied to produce L-lactate in optically pure form (i.e., in which essentially only the L-form of lactate is produced).

As indicated above, the amount of free lactic acid present in a solution is a function of both the pH of the solution and the overall concentration of lactate material (i.e. lactic acid plus dissolved lactate salt) in the mixture. Thus, specifying these two parameters for a given solution (e.g., a fermentation broth), effectively specifies the free lactic acid concentration. The process of Carlson et al typically generates a solution containing at least about 50 g/L, preferably at least about 80 g/L, and more preferably at least about 100 g/L lactate salt/lactic acid at a relatively low pH. The lower the solution pH, the higher the percentage of the lactate material which is present in the free acid form. Again, if the medium (solution or mixture) pH is equal to the $pK_a$ of lactic acid (which is about 3.8 at 25° C.), 50% of the lactate material is present in the free acid form.

The pH of the nutrient medium during the homolactic bacterial incubation step can be expressed in several different ways, e.g., in terms of the average incubation pH or the final incubation pH. The fermentation process of Carlson et al is typically capable of producing high levels of lactate material at an average incubation pH of no more than about 4.3, preferably no more than about 4.2, and more preferably no more than about 4.0.

Alternatively, the pH of the broth during incubation can be expressed in terms of the final incubation pH. The process of Carlson et al typically allows the production of high lactate concentrations at a final incubation pH (or mixture pH) of no more than about 4.2, preferably no more than about 4.0, and more preferably no more than about 3.9. Particularly effective embodiments of the fermentation process described in Carlson et al are capable of generating solution containing at least about 100 g/L lactate material at an average incubation pH of no more than about 4.0 and/or a final incubation pH of no more than about 3.9.

Herein the terms "nutrient medium" and "fermentation broth" are used interchangeably. Both are mixtures of free lactic acid and lactate anion (salt). These terms may be used to refer to: (i) media in the form originally provided, for example to the acid-tolerant bacteria and the sources of nutrient including carbohydrates; (ii) media produced after some or all of the originally provided nutrients have been consumed and fermentation products including lactate have been excreted into the media by the bacteria; and, (iii) clarified media after removal from a fermentor and filtration.

The process provided in Carlson et al for producing lactic acid includes incubating acid-tolerant bacteria, such as acid-tolerant homolactic bacteria, in nutrient medium at a pH which furnishes a substantial portion of the lactate material in the free acid form. Herein, when the term "acid-tolerant" is employed in reference to bacteria, the intent is to refer to bacteria which are capable of producing lactate material at a pH sufficient to furnish a substantial portion of the lactate material in the free acid form. The acid-tolerant bacteria described in Carlson et al are typically capable of producing at least about 25 g/L free lactic acid. Such bacteria generally can also produce at least about 50 g/L lactate material in nutrient medium at an average incubation pH of no more than about 4.2. If fermentation is carried out to a point where pH and/or lactic acid concentration inhibits further lactate production, the "average incubation pH" is determined based on an average of the pH values measured at ten( 10) or more equal time intervals over the time period necessary to produce 90% of the limiting lactate concentration. The fermentation process may be run in a continuous fashion. Under such conditions, steady state conditions (in terms of pH, lactate concentration and nutrient concentrations) are generally achieved and maintained after an initial startup phase has been concluded. When fermentation is conducted in this manner, the average incubation pH is the average pH of the broth after the initial startup phase has been completed.

If fermentation is not carried out to a point where the limiting lactate concentration is reached, the "average incubation pH" is determined based on an average of the pH values measured at ten(10) or more equal time intervals over the course of the fermentation. As used herein, the "limiting lactate concentration" is the lactate concentration (concentration of undissociated and dissociated lactic acid) under a given set of incubation conditions (nutrient medium, temperature, degree of aeration) at which pH and/or lactic acid concentration generated by the fermentation inhibits further lactate production. As used herein, the term "limiting incubation pH" means the pH of the fermentation broth for a given set of incubation conditions at which the pH and/or lactic acid concentration inhibits further lactate production. Inhibition of lactate production is considered to have occurred when the amount of lactate produced in a batch fermentation does not increase by more than about 3% upon further incubation for a period of up to about twelve (12) hours under the same conditions. This definition presumes that sufficient nutrients for lactate production are still available in the fermentation broth and applies to both batch and continuous operations.

In the process of Carlson et al, the pH of the fermentation broth after incubation of the acid-tolerant bacteria to produce lactate is typically no more than about 4.2 ("final incubation pH").

As referred to herein, the "final incubation pH" is the pH of the fermentation broth at the point that growth and/or lactate material production by the acid-tolerant bacteria ceases. The cessation of growth and/or lactate material production may be the result of a change in reaction temperature, the exhaustion of one or more necessary nutrients in the fermentation broth, a deliberate change in pH, or the separation of the fermentation broth from the bacterial cells. In those instances in which fermentation is deliberately stopped by the addition to the fermentation broth of sufficient acid or base to stop lactate production, the final incubation pH is defined to be the pH of the nutrient medium just prior to the addition. Alternatively, growth and/or lactate material production may stop due to the accumulation of one or more fermentation products and/or a change in broth pH resulting from the production of fermentation products, i.e., the fermentation reaction has reached a self limiting point for the given set of incubation conditions. As noted above, it is quite common for bacterial fermentations which produce an organic acid such as lactic acid to be subject to end-product inhibition.

The term "lactate material" as used in this application refers to 2-hydroxypropionate in either its free acid or salt form. The terms "lactic acid" and "free lactic acid" are employed interchangeably herein to refer to the acid form, i.e., 2-hydroxypropionic acid. The salt or dissociated form of lactate is specifically referred to herein as a "lactate salt," for example, as the sodium (or calcium) salt of lactic acid or sodium lactate (or calcium lactate).

III. Separation from the Fermentation Broth—Lactate vs. Lactic Acid

A variety of issues are presented upon development of a processing approach for lactate/lactic acid solutions involving generation of large amounts of lactic acid; for example, in solution at pHs no greater than about 4.8 (preferably no greater than about 4.2 or 4.3) from the fermentation broth; and, with a concomitant isolation (and if desired recycling) of lactate salt (typically calcium lactate, potassium lactate, sodium lactate and/or ammonium lactate). The principle concerns relate to design of the system to accommodate the two objectives of:

1. Isolation of lactic acid products for follow-up processing, for example to generate polymer; and
2. Isolation of lactate salt, preferably in a form desirable for recycling to the fermentation broth.

Three general approaches concern:

1. Separation of the lactic acid from the solution leaving the lactate salt behind; and, if desired, direction of the residual solution having the lactate salt therein, after the separation, into a fermentor;
2. Isolation of the lactate salt from the solution; direction of the lactate salt, if desired, into a fermentor; and, a follow-up isolation of the lactic acid product from the residual solution after lactate salt separation; and,
3. Simultaneous separation of lactic acid into one stream and lactate salt into another, leaving residual mixture.

With the techniques described herein, each is possible. However, advantageous overall processes will depend, in part, upon selection, among the approaches, of the one which most readily facilitates an overall cost-effective and efficient processing scheme in large scale implementation.

The techniques herein can be practiced on a variety of solutions of lactate material (i.e. solutions of lactic acid and dissolved lactate salt). These solutions may comprise fermentation broth or broth which has been removed from a fermentor and modified in some manner, for example by filtration or pH adjustment. Indeed the techniques can be applied to the solutions which are made in other manners as well. The techniques and proposals described herein, however, are particularly developed with a focus on efficient processing of fermentation broth solutions, especially relatively acidic ones, in which pH modification by addition of acid is not required and preferably has not occurred.

Although the techniques described herein are particularly well suited to processing selected bacterial fermentation broths, they can be applied to other mixtures of lactic acid such as those obtained from: fungal or yeast action; purge streams from lactide reactions; or, polylactic acid streams from polylactic acid processing.

As disclosed in the Carlson et. al., patent application, incorporated by reference above, alternative approaches to producing lactic acid based on the fermentations of other more acid tolerant microorganisms have also been reported. Yeasts, such as *Saccharomyces cerevisiae*, are capable of growth at much lower pH than lactobacillus. Recombinant yeast stains have been produced by introducing the lactate dehydrogenase gene from a bacterial (lactobactobacillus) or mammalian (bovine) source into *Saccharomyces cerevisiae*. The recombinant yeast strains are reportedly able to produce lactate at or below the $pK_a$ of lactic (about 3.8). Lactic acid production by a pellet form of the fungus, *Rhizopus orgyzae*, has also been reported.

Typical compositions in which techniques according to the present invention can be applied, with respect to pH, would be at least 0.86 and less than 6.0. That is, typical compositions on which the techniques will be practiced, will have a pH within this range. As indicated by Equation 1, and FIG. 11, for such compositions the molar ratio of free lactic acid to dissociated acid or dissolved lactate salt at 25° C., is within a range of about 1,000:1 to 0.007:1. More preferred processing will involve solutions with a pH in the order of about 1.98–5.00 (HLA:LA ratio within the range of about 75:1 to 0.070:1); and, most preferred processing will involve solutions having a pH within the range of about 3.0–4.5 (HLA:LA ratio within the range of about 7.0:1 to 0.23:1).

As indicated above, with preferred processing described in Carlson et al, solutions within the most preferred pH range described above are readily obtained, with substantial concentrations of the lactate material therein. Alternatively, other fermentation broths can be used, for example with pH adjustment by addition of acid typically to the most preferred pH range given. Certain preferred methods of acidulation are described hereinbelow.

Herein, there will sometimes be reference to "preferential separating" of: lactic acid from a composition containing lactic acid and lactate salt; or, lactate salt from composition containing lactic acid and lactate salt. The term "preferential separating" and variants thereof, in this context, is meant to refer to separation technique which preferentially removes one of the two components (lactic acid or lactate salt) with respect to the other. In typical preferred processing according to the present invention a mixture of lactic acid and lactate salt is divided into two "product streams". In one product stream, (i.e., the free lactic acid rich stream), preferably the molar ratio of free lactic acid to lactate salt obtained is at least 2/1 and preferably at least 3/1. With certain of the techniques described herein, ratios of at least 5/1 and indeed in ratios of 10/1 or more are readily obtainable.

The other product stream is the lactate salt rich stream. In this stream, preferably the molar ratio of free lactic acid to lactate salt is no greater than 0.5. With typical preferred processing as described herein ratios of no greater than 0.3, preferably no greater than 0.2 and most preferably 0.1 or lower are readily obtained.

Herein the term "stream" when used in the context indicated by the previous two paragraphs, is meant to refer to an isolated phase or product segment, without regard to whether that phase or product segment is a solution, solid or a mixture of materials. Thus, a "lactate acid rich stream" is merely a phase or mixture rich in lactic acid (versus lactate salt) by comparison to the original mixture processed; and, a "lactate salt rich stream" is a stream rich in lactate salt (versus lactic acid) by comparison to the original mixture processed.

When the product stream enriched in free lactic acid is obtained as a result of separating the free lactic acid from the mixture, for example from a fermentation broth, the remaining aqueous mixture after the free lactic acid removal will sometimes be referred to as "depleted" with respect to free lactic acid. Similarly, when the lactate salt enriched stream results from separation of the lactate salt from a mixture containing the free lactic acid and the lactate salt, the remaining mixture will sometimes be referred to as "depleted" with respect to the lactate salt.

Preferably, when the solution processed is a fermentation broth, the product stream enriched in lactate salt is provided and formed such that the weight ratio of impurities from the fermentor, to lactate salt therein, is lower than found in the fermentation broth, preferably by a factor of at least 5. This can be managed by techniques described herein concerning control over the particular approach selected for isolation of the lactate salt, as well as through use as various purification techniques, such as back washing or recrystallization. Preferably, the lactate product stream is eventually isolated as an aqueous solution or mixture of an aqueous phase and a solid phase, for convenient recycling into a fermentation system, in order to maintain water balance. If concentration of an aqueous solution is used in order to facilitate the water balance in the broth, preferably relatively low-cost concentration techniques such as reverse osmosis and vapor recompression are used.

IV. Various Options for Lactic Acid/Lactate Salt Separation; Advantages and Disadvantages

A. Removal of Lactic Acid from the Fermentation Broth (or Other Lactic Acid/Lactate Salt Mixture).

A class of advantageous processing approaches involves removal of the lactic acid from the fermentation broth or other mixture, while leaving the soluble lactate salt behind in the fermentation broth. (The separation can, in some instances, occur within the fermentor or it can be conducted on solution material removed from the fermentor.) If, after such separation, the residual fermentation broth can then be recycled, one can also preserve at least part of the various nutrient values in the broth, for use in the feed.

A number of approaches can be used for preferentially separating lactic acid from a fermentation broth (or other mixture) including such materials as lactate salt and other dissociated salts therein. The approaches include the following:

1. Extraction. It is possible to remove the lactic acid from a lactic acid/lactate salt mixture such as a fermentation broth, by extraction. For example, extraction can be conducted with a water insoluble amine, preferably amines having at least 18 carbon atoms, most preferably tertiary amines, see for example U.S. Pat. Nos.: 4,771,001; 5,132,456; and 5,510,526; and Shimizu et al, *J. of Fermentation and Bioengineering* (1996), Vol. 81 pp. 240–246; Yabennauor and Wang, *Biotech Bioeng.*, (1991) Vol. 37, p. 1095–1100; and, Chen and Lee, *Appl. Biochem. Biotech*, (1997), Vol. 63–65, pp. 435–447. These six references are incorporated herein by reference. Extraction of the lactic acid is a favored approach when the lactic acid partitions between two immiscible liquid phases. The scale-up and performance of extraction processes is straight-forward. Extraction processes are favorable due to the lack of solids handling, the wide variety of equipment available for contacting two immiscible phases, and the ability to handle large flow rates. Extraction processes can suffer when the phases tend to form stable emulsions or have a high viscosity. One also has to be concerned about: (a) entrained and soluble solvent components affecting the productivity of the microbe; and (b) the extraction process removing important nutrients from the recycled broth.

The extraction process can be performed in the fermentor, in an outside contactor, or with the use of a membrane to keep one phase from being dispersed in the other. The use of a supported liquid membrane can be useful depending upon the overall separation process.

The choice of the extraction solvent is important to the overall efficiency and economics of the separation process. A measure of extraction efficiency is the partition coefficient as calculated by the concentration (wt. basis) of lactic acid in the organic phase (extractant) divided by the concentration of the lactic acid in the aqueous phase (phase from which extraction occurs). It is desired to have a partition coefficient greater than 0.1, even more desirable is a partition coefficient greater than 1.0, and even better if the partition coefficient is greater than 3.0. This latter can be accomplished by selecting the appropriate solvent or mixture of solvents from the following preferred solvents. Of course in commercial scale practice, extraction efficiency is the ability to achieve a combination of high yield, low extractant volume, and concentrated product. This can be accomplished with the techniques discussed herein.

Solvents that give favorable partitioning include: oxygenated solvents, phosphate esters, phosphine oxides, amines, and mixtures of these solvents. Oxygenated solvents that are suitable include alcohols, ketones, ethers, esters, acids or solvents that have a multiple number of these functional groups. Solvents including at least 60% by wt., more preferably at least 80% by wt. and most preferably at least 90% by wt. (typically 95% or more), component(s) which is (are) generally water immiscible (solubility not more than about 50 grams per liter in water at 25° C.) are preferable. Specific usable solvents are 1-butanol, 2-ethyl hexanol, 1 -octanol, methyl isobutyl ketone, cyclohexanone, disobutyl ketone, isopropyl ether, ethyl acetate, isobutyl acetate, ethyl lactate, butyl lactate, octyl lactate, N.N-dibutyl lactamide, and hexanoic acid. Suitable phosphate compounds include tributyl phosphate, triphenyl phosphate, diethylhexylphosphoric acid, and trioctylphosphine oxide. Suitable amines include triethylamine, dioctylamine, trioctylamine, tridecylamine, methyl didodecylamine and industrial preparations such as Amberlite LA-1 (a dialkyl amine mixture with twelve carbon atoms in each alkyl chain), Alamine 304 (tridodecylamine), Alamine 308 (a trialkyl mixture of branched chains with a total of 8 carbon atoms on each chain), and Alamine 336 (a commercially available mixture of trioctyl⁻; tridecyl⁻; dioctyldecyl⁻ and didecyloctyl amines). The extracting solvent may also preferably contain a hydrocarbon fraction, such as kerosene, typically (if used at all) at 1 to 40% by wt. Such a hydrocarbon fraction favorably modifies the viscosity, phase coalescence, and other physical properties of the system. One useable, and often preferred, solvent system comprises, by wt., 0 to 15% ethanol; 65 to 85% Alamine 336 and 15 to 35% kerosene.

Depending upon the lactic acid product of interest, the solvent characteristics will be varied. If the lactic acid product of interest comprises lactic acid oligomers, a solvent with a relatively low boiling point by comparison to lactic acid oligomers/lactic acid (preferably less than 200° C. at 760 mm Hg) is advantageous because the solvent can be easily vaporized and separated from the lactic acid oligomers. If the lactic acid product is an alkyl lactate ester such as methyl lactate, a solvent with a relatively high boiling point by comparison to the ester(s) (preferably greater than 175° C. at 760 mmHg) is advantageous to easily distill the methyl lactate away from the solvent.

Also, when making a lactate ester, it may be advantageous for the alcohol of that ester to be a component in the extracting solvent. If the product is a lactic acid amide, it may be useful to have the corresponding amine present. Conversely, if the product is lactic acid, the presence of an alcohol or non-tertiary amine in the solvent may be unfavorable due to the possibility of yield loss in the formation of esters or amides.

2. Adsorption. Another approach to isolation of lactic acid from a fermentation broth including free lactic acid and dissolved lactate salt is through: adsorption of the lactic acid onto a solid adsorbent; follow-up physical separation of the solid adsorbent from the liquid phase; and, eventual generation of the lactic acid from the solid adsorbent. (Herein the term "adsorption" is intended to include within its scope absorption. That is, the specific mechanism of interaction is not referenced, unless otherwise specified.)

The partitioning of the free lactic acid into a solid phase either by ion exchange or adsorption is another favorable method for separating lactic acid from an aqueous solution. These methods show good efficiency when the solid phase has a high capacity for lactic acid, an efficient regeneration cycle, and long life time in the process. Excessive pressure drop over a solid bed, bed swelling, possible dilution of product upon regeneration, resin fouling and slow mass transfer rates can make solid phase processes difficult.

The capacity of the resin is an important characteristic of the resin because it determines, along with the mass transfer rate, how much resin is required for a given amount of lactic acid. A resin with a capacity of 0.10 g lactic acid per g dry resin would be suitable, a capacity of 0.20 g lactic acid per g dry resin is better, and a capacity of 0.30 g lactic acid per g dry resin is best. This latter can be accomplished for example with Dowex MWA-1 resin in equilibrium with a 20 g/liter lactic acid solution having a pH of no more than 4.5 at room temperature.

Contacting a solid phase with the aqueous lactic acid solution can occur in the fermentor or in equipment outside the fermentor. For contact inside the fermentor, the microbes are immobilized and the solid phase adsorbent is separated from the microbes on the basis of differences in falling velocity in a fluidized bioreactor; See for example, Davidson and Scott, *Biotechnology and Bioengineering,* (1992), Vol. 39, pg. 365–368, incorporated herein by reference.

Ion exchange resins that would be suitable for lactic acid recovery are weak, moderate, and strong basic anion exchangers. As the pH of the aqueous lactic acid stream increases, a stronger basic anion exchanger is required to recover the lactic acid. Therefore, the pH of the lactic acid stream will be one factor in the choice of ion exchange resin. Commercially available tertiary amine ion exchange resins that would be suitable include Reillex 425 and Reillex HP (both poly-4 vinylpyridine resins, Reilly Industries, Inc. of Indianapolis, Ind.), Dowex MWA-1 and Dowex 66 (both polystyrene-divinylbenzene tertiary amine resins, Dow Chemical Company of Midland, Mich.), and Duolite A561 (an acrylic-divinylbenzene tertiary amine copolymer), and Amberlite IRA-67 (a crosslinked phenol-formaldehyde-tertiary amine resin) (Rohm and Haas Corp. of Philadelphia, Pa.). Both macroreticular and gel resins are suitable.

Another factor of importance in the choice of resin is the technique available for removing the lactic acid from the resin. As the basicity of the resin increases, the regeneration method must be more "powerful" to remove the lactic acid from the resin. A suitable regeneration method would be to contact the resin with a polar liquid possibly at an elevated temperature. Suitable polar liquids include water, aqueous solutions, methanol, ethanol, triethylamine, methyl isobutyl ketone, dimethyl sulfoxide, N-methylpyrrolidinone, 1,4-dioxane, tributyl phosphate, trioctylphosphine oxide, and various combinations thereof. Evaporation of the lactic acid product is potentially a method as well. In the case of evaporation, thermally stable resins, like the Reillex ones are very useful. King et al disclose the use of aqueous trimethyl amine solutions to regenerate adsorbents and distill of water and trimethylamine to isolate lactic acid in U.S. Pat. No. 5,132,456, incorporated herein by reference.

The selectivity of the resin is also important since preferably, the resin should be selective for the lactic acid and not the nutrients needed by the microbes. The resin may also need to be washed with solvents, acids, and/or bases prior to use to minimize any leaching of monomers, oligomers, or other compounds that may be toxic to the microbes.

3. Separation by Vaporization. Distillation of the lactic acid from the aqueous solution or mixture is an alternative method of separation. This method would not contaminate the recycle stream with residual extractant material that may be toxic to the microbes and it allows good water balance control. A disadvantage of this approach is that water needs to be distilled first. This is energy intensive; and, as water is removed, conditions are favorable for lactic acid condensation.

Vacuum conditions for the distillation (i.e. less than 300 mm Hg), to lower the temperature of the distillation will be preferred because lactic acid condensation to dimer or oligomer, is reduced. Lactic acid recovery can be facilitated by using equipment such as a thin film evaporator that minimizes the residence time of the monomer during the distillation. One possibility is to add an alcohol such as ethanol and make ethyl lactate, which has a greater volatility compared to lactic acid, and therefore is easier to distill.

4. Separation via Membrane. Lactic acid can pass through a membrane into a separate aqueous phase. This method will be favorable if the membrane chosen is one which is highly selective for lactic acid (versus lactate salt). A useful membrane is a dense hydrophilic membrane such as Celgard 3400 from Hoechst Celanese Co. of Somerville, N.J. and anion exchange membranes that also allow proton transfer.

An example of this type of process is to have an ammonia solution across the membrane from the lactic acid solution. The lactic acid is driven across the membrane to neutralize the ammonia The ammonium lactate solution could then be subjected to conditions that vaporize the ammonia giving a lactic acid solution. Other volatile bases such as trimethylamine or triethylamine could be used alternatively. The use of a strong base, such as sodium hydroxide, would typically undesirably neutralize the lactic acid to sodium lactate. Thus, in general with such an approach, a weak base should be used on the opposite side of the membrane from the fermentation broth. That is, a weak base, such as the amine bases mentioned above, will form an association that can be readily disassociated to regenerate the lactic acid.

The term "weak base" as used herein is meant to refer to a base with a pH of half neutralization of less than 2.5; a "moderate" base will be considered to be a base with a pH of half neutralization of between 2.5 and 7.0; and a "strong" base will be considered to be a base with a pH of half neutralization of greater than 7.0. The term "pH of half neutralization" is a measure of apparent basicity of a water immiscible base, as defined in Grinstead, R.R. et al., *J. Phys. Chem.,* Vol. 72, #5, p. 1630 (1968), incorporated herein by reference.

No matter which method is used for removal of the lactic acid from the fermentation broth, the follow-up fate of the lactate salt and residual fermentation broth needs to be considered. Of course, it would be preferable to use a technique which leaves the residual fermentation broth and lactate salt in a desirable form for direct recycling, without further significant treatment. On the other hand, it may be desirable to isolate the lactate salt from the residual broth, so that the lactate salt can be recycled or otherwise used, with the fermentation broth either directly recycled, or disposed of or used in other manners. Various approaches to removal of the lactate salt from the residual fermentation broth, after lactic acid removal, include: extraction; electrodialysis; ion exclusion; adsorption with a solid adsorbent, with follow-up separation from the adsorbent; separation with membrane; and, crystallization.

It is noted that in some instances the techniques involved may lead to addition of a material to the recycle stream, having the lactate salt in solution. For example, extraction methods may affect the composition of this stream. When such approaches are chosen, it is important to either use materials that will have low toxicity to microbes, or to develop follow-up treatments which modify the composition of the stream appropriately for recycling, for example by flashing the volatile compounds from the residual broth or contacting the broth with a low toxicity immiscible liquid that extracts toxic components. A preferred method would be to use a low toxicity immiscible liquid as the extracting solvent or as a component in the extracting solvent and as the immiscible liquid used to extract out the toxic components.

The techniques described in this section can be practiced in a continuous or a batch manner. Indeed even the feed flow from the fermentor, and fermentor operation, can be practiced continuous or batchwise.

B. Removal of Lactate Salt from Fermentation Broth—Leaving Lactic Acid Behind As indicated above, an alternate approach to lactic acid production involves separation of lactate salt from the fermentation broth (or other mixture), leaving the lactic acid behind in the residual mixture, with later processing of lactic acid from the residual mixture. The isolated lactate salt could be useful, for direction (or recycling) to the fermentation system for pH control, if desired.

A variety of approaches can be used for isolation of lactate salt, from a fermentation broth or other lactic acid/lactate salt mixture, leaving the lactic acid behind. These could, in general, be developed around the same approaches as characterized in the previous section for isolation of lactate salt from the residual fermentation broth after lactic acid removal. As with the approaches of the other section, they can be practiced in a continuous or a batch manner. The approaches, then, would generally be the following:

1. Extraction. A lactate salt can be extracted from an aqueous solution containing lactic acid with the use of a quaternary amine such as methyl trioctyl ammonium chloride or a mixture of methyl trialkylammonium chloride salts such as ALIQUAT 336 (the corresponding methyl ammonium chloride of Alamine 336 available from Henkel Corp. in Kankakee, Ill.). Typically, methyl trialkyl ammonium halide (preferably chloride) salts of trialkyl amines of 18 carbons or more are used. In general an anion exchange occurs, in which the lactate anion is exchanged for the chloride anion present in the amine phase. Thus, this approach can "load" the residual solution, containing the lactic acid therein, with chloride ion.

Another extraction approach is to fully extract the lactate salt using a coupled extractant consisting of both a liquid cation and liquid anion exchanger in a solvent. An example would be the use of quaternary amine as listed above with diethylhexylphosphoric acid. The lactate salt is extracted with the formation of water. The quaternary amine may need to be pretreated to the free base form of the amine for this to work efficiently.

2. Solid Adsorbent. The fermentation broth containing both the lactic acid and lactate ion could be contacted with a solid adsorbent, for removal of the lactate ion. Preferred solid adsorbents for this would be strong anion exchangers such as fixed quaternary ammonium compounds. An example would be Amberlite IRA400 and Amberlite IRE-900 available from Rohm and Haas Co., Philadelphia, Pa. Such materials generally comprise quaternary ammonium functionality and styrene divinyl benzene copolymer.

Another approach would be to use mixed bed ion exchange resins to separate the lactate salt from the aqueous solution. This is similar to the mixed liquid ion exchangers mentioned above.

Another approach to separate the mixture using a solid adsorbent is the technique of ion exclusion. In ion exclusion chromatography, an anion exchange resin is converted to the lactate form. The lactate anion in the feed solution comes out with the void volume of while other ionic components are retained by the resin.

3. Separation with a Membrane. The lactate ion can also be removed from an aqueous solution such as a fermentation broth, leaving a lactic acid behind, by electrodialysis. More specifically, the fermentation broth, preferably prefiltered, and a relatively pure water stream are fed to an electrodialysis unit. The unit would include alternating cation and anion exchange membranes forming a plurality of compartments (or stack) with a cathode and anode at opposite sides of the stack (for providing an electric field through the stack). The properties of the membranes would be such that substantially only anions would pass through the anion exchange membrane and only cations pass through the cation exchange membranes. An electrodialysis unit for water desalination would be suitable for separating and concentrating the lactic salt, and providing a lactic acid rich/lactate salt depleted stream. Companies such as Aqualytics in Warren, N.J. and Ionics, Inc. in Watertown Mass. provide desalination equipment appropriate for this use.

4. Crystallization. Lactate salts can be crystallized from aqueous solutions. Thus, the lactate salt can be removed from the fermentation broth (or other mixture) via a crystallization process. This can be done through concentration (for example, by evaporation of the water); by reduction in temperature and/or by addition of agents to facilitate the crystallization (for example water soluble alcohols such as $C_1$ to $C_4$ alcohols (methanol, ethanol, propanol, and/or the various butanols). After the physical separation of the crystallized product from the solution, the remaining lactic acid containing solution could then be further treated for isolation of the lactic acid.

In certain preferred processing, the added agent is preferably one which has a low solubility in water at about ambient temperature, but this solubility increases sharply upon an increase in temperature. Butanol provides a good example. Addition of butanol to a lactic acid and lactate salt containing solution at an elevated temperature, about 100° C., and under appropriate pressure to avoid vaporization, would result in the efficient crystallization of the lactate salt. This type of agent has many advantages. First, it is relatively easy to separate from the remaining solution after the crystallization, for example by cooling. Second, upon cooling of the liquor after lactate salt crystallization, the lactic acid will distribute between the two phases (water and butanol) forming a very efficient combination of crystallization and extraction in one operation. That is, the lactate salt is crystallized and the lactic acid is extracted into butanol. Third, if the added agent is an appropriate alcohol, a lactate ester can be formed and separated in a pure form, for example by distillation.

If crystallization is the selected approach, calcium lactate (CaLa$_2$) will often be the selected salt because: (a) it has a relatively low solubility in water; and (b) its solubility in water is strongly dependent on temperature. The calcium lactate salt can be provided by use of the appropriate soluble calcium salt, such as calcium carbonate, to the mixture.

Of course, whatever approach is used to isolate the lactate from the mixture, the overall processing scheme will require recovery of the lactic acid value, in some form, from the residual broth (or other mixture) after the lactate salt removal. Approaches analogous to those described above, with respect to removal of lactic acid from a fermentation broth or other mixture, can be used. More specifically: extraction; solid adsorption; vaporization; or membrane separation as described previously, are feasible. For many of these options, a step of previous separation of the lactate salt will be beneficial, because in some instances acid separation will be more efficient when conducted without the buffering effect of the lactate salt. Thus, the techniques described above for lactic acid recovery would be applied to a lactate depleted solution, to achieve lactic acid purification/isolation rather than separation from lactate.

V. One Preferred Class of Approaches—Lactic Acid Removal from the Mixture by Extraction In some instances, a preferred class of approaches to overall processing will involve lactic acid separation from the mixture via extraction. Among the reasons for this are the following:

1. With an extraction process, especially if practiced on a clarified fermentation broth or similar solution, it may be possible to leave the residual lactic acid depleted solution, with the lactate therein, in an appropriate form for recycling into the fermentor without substantial further treatment, other than perhaps a diluent wash or similar treatment to remove any residual extractant that may be toxic to the microorganisms of the fermentor.
2. Extraction processes can be conducted, in many instances, efficiently and rapidly on a large scale.
3. Extraction processes can be quite selective for the lactic acid, versus other materials (such as amino acids and carbohydrates) in the fermentation mixture. Such high selectivity can be achieved using basic extractants such as trialkylamines, especially relatively insoluble trialkylamines having at least 18 carbon atoms, such as Alamine 336.

A variety of approaches can be used for lactic acid recovery, i.e., the removal of the lactic acid values, or lactic products, from the lactic acid containing extract. Approaches include the following:

A. Phase-Splitting. In general, when applying this technique, the extractant containing the lactic acid is modified to generate lactide and/or lactic acid oligomers. This would be done, for example, by driving the condensation reaction (lactic acid to dimer or oligomer) through evaporation of water, during concentration. To facilitate such a follow-up process, a hydrophobic extracting solvent for the original extraction is preferred, since most of the separation of the lactic acid from the water of the original aqueous phase (e.g. fermentation broth) will have been done by the extraction step and phase separation. An example of a suitable hydrophobic extracting solvent is one with a high proportion of long-chain alkylamines and at least 1–35% kerosene, by wt. Those extracting solvents typically coextract only one mole of water per mole of extracted lactic acid. The condensation reaction (to form lactide or oligomer) can be facilitated by catalyst addition. In general, during condensation/concentration the resulting lactide or oligomers will form a separate phase from the remainder of the extractant, for example, the amine. Physical separation can then be used to accomplish recovery of the desired lactic product. The separated oligomer can then be taken directly to lactide, without removal of residual extractant therein, if desired.

It is noted that this approach, especially when an amine is used as the extractant, can lead to some degree of racemization of the lactic product. The racemization can be minimized through use of low temperature, low pressure conditions for the condensation reaction. For example, below 150° C. and below 20 mmHg.

B. Extraction. With this approach, one back extracts the lactic acid from the first extracted phase. This can often be done with an aqueous extraction or wash, due to the high solubility of lactic acid in water. Of course, other polar liquids such as dimethylsulfoxide (DMSO), N-methylpyrrolidinone, N,N-dimethylforamide (DMF), triethylamine, and lactide can be used. In some instances it may be desirable to use relatively warm back extraction conditions by comparison to the first extraction, for example back extraction with water at a temperature of at least 100° C., typically about 150° C. or higher, to facilitate the process. (Assuming conditions of the first extraction of 15°–60° C. at atmospheric pressure.) Such a back extraction would typically be conducted under a pressure of at least 30 psig.

C. Membrane Separation. Membrane separation techniques can be used to facilitate separation of the lactic acid from the lactic acid—extracting solvent phase. For example, one could use a hydrophilic barrier with the extractant phase on one side and a preferred phase for the lactic acid on the other. This preferred phase could, for example, be a tertiary amine such as described above for membrane separation for lactic acid from the fermentation broth. In some instances, aqueous systems can be used.

D. Distillation of Solvent. If the solvent of the extractant phase is of relatively low molecular weight or high volatility, for example butanol, it can be distilled or flashed from the extractant phase, leaving lactic acid behind. This approach will be most useful when the extractant phase comprises such solvents as: butanol, methyl isobutyl ketone or triethylamine. It may be desirable to use relatively low pressure conditions to facilitate the distillation. For example, processing at pressures on the order of about 500 mm Hg or below will be preferred. The use of a carrier gas and of pervaporation are also preferred. In some instances the lactic acid concentration which occurs during distillation will lead to formation of condensation products such as lactate esters (if alcohols are present), lactide or lactic acid oligomers.

E. Distillation of Lactic Product. Distillation of lactic product, for example lactic acid, from the extractant phase will be favored when the extractant phase comprises a material of relatively low volatility. For example, when tertiary amine, especially tertiary amines of 18 carbon atoms or more, is used in the extractant phase, distillation can be readily used to recover the lactic acid. With respect to this, attention is directed to U.S. Pat. No. 5,510,526 incorporated herein by reference.

Of course, in some instances, the extraction phase may contain materials of both high volatility and low volatility. When such is the case, multi-staged distillations may be preferred, to obtain isolation of lactic acid or lactic product. Here again, a carrier gas and particularly pervaporation could be advantageous.

F. Crystallization of Lactic Product. When the lactic acid product is lactide, a favorable approach to separation from the extracted phase is crystallization. More specifically, lactide crystallizes readily from non-polar solvents such as toluene.

It will typically be desired to generate lactide from the recovered lactic acid in the extraction. This can be done by water removal and condensation under controlled conditions. See for example, U.S. Pat. No. 5,142,023 incorporated herein by reference, with respect to lactide formation.

G. Aqueous Extraction, Solvent Re-extract. With this approach, the lactic acid is extracted from the extractant phase into an aqueous phase. It is then removed from the aqueous phase into a preferred extractant phase for follow-up processing, such as condensation to oligomer and eventual processing to lactide. A typical example would be a first extraction into a tertiary amine phase, preferably amines of 18 carbons or more, with a follow-up extraction from the tertiary amine phase into an aqueous phase. The lactic acid can then be extracted into cyclohexanone or another non-amine, polar, solvent, with the condensation (to oligomer) occurring in the cyclohexanone (or other non-amine, polar, organic solvent) during concentration/distillation. The temperature of the back extraction into the aqueous phase can be higher than the temperature during extraction into the organic phases. This is preferred to condensation within the tertiary amine phase directly, if racemization is to be minimized or avoided.

Of course, the lactic acid could be isolated from the aqueous phase directly, for example, by distillation of the water. However, in general, this may require more energy than condensation within a preferred polar organic phase of higher volatility.

VI. Various Approaches to Separation of Lactic Product from an Extracted Phase—a Closer Look The following describes a typical approach to the problem of making lactic acid products from a lactic acid fermentation or other aqueous lactic acid solution, using the techniques described above. Assume a broth comprising about 50 to 110 g/liter total lactic material at a pH of 3.5 to 4.3. The broth is withdrawn, continuously, from a fermentor. The broth is clarified to remove coarse impurities and other insolubles in the stream, for example by passage through a filter (or through flocculation, centrifugation or a combination of those various techniques). This filter may be a dead-end filter or a cross-flow filter using micro- or ultra-filtration membranes. (In some instances, pretreatment with activated carbon may also be conducted to purify the mixture.) The undissociated lactic acid is then extracted from the broth or remaining lactate salt solution. The extracting solvent includes a tertiary alkylamine, an oxygenated solvent that increases the partition coefficient, and a kerosene fraction that modifies the viscosity of the solvent mixture. Preferably the extracting solvent contains 60 to 80 wt % tertiary alkylamine, such as Alamine 336, 5 to 20 wt % methyl isobutyl ketone, and 10 to 30 wt % kerosene (for example IsoPar K). The aqueous lactic acid solution and extracting solvent are contacted in a countercurrent fashion in either: an agitated column; a packed column; a perforated plate column; a raining bucket contactor; a centrifugal contactor; or, mixer/settler equipment. The temperature during this contacting is between 0° C. and 95° C., but more preferentially between 15° C. and 60° C. The exiting streams from the extraction process are a lactate salt aqueous solution and a lactic acid-rich extract. The lactate salt aqueous solution is recycled back to the fermentor. The lactic acid-rich extract would then be processed in order to make the lactic acid products generally referenced above.

To make a nearly pure lactic acid stream, the lactic acid product in the extract should be separated from the solvent in order to regenerate the solvent and isolate the lactic acid product. As indicated above, there are a number of methods to separate the lactic acid from the solvent. For example, the lactic acid product can: be extracted into a second phase of low miscibility with the extracting solvent; distilled with either the solvent or the lactic acid product going overhead; or passed, through a membrane to another phase. In another method, all or some of the extracting solvent can be distilled off while adding a second, less volatile, solvent in order to get the lactic acid in a different solvent composition. This method was disclosed by Verser, et al. in U.S. Pat. No. 5,420,304, incorporated herein by reference.

A preferred separation scheme to obtain lactic acid from the extracting solvent is to distill the lactic acid/extracting solvent stream to get a crude lactic acid stream. There may be components in the extracting phase that are both higher boiling and lower boiling than the lactic acid. Efficient and economical distillation schemes of these components can be conducted with conventional distillation equipment. In a preferred method, high vacuum and high surface area equipment are used to isolate lactic acid efficiently with a minimum amount of condensation. A wiped film evaporator or a falling film evaporator would be suitable for this type of operation.

A vaporized lactic acid stream could be condensed to form a concentrated liquid lactic acid stream that can be further processed to lactic acid oligomers and lactide in processes described by Gruber, et al. in U.S. Pat. No. 5,142,023. A vaporized lactic acid stream can be contacted with an appropriate catalyst to form lactide as described by Bellis and Bhatia in U.S. Pat. No. 5,138,074, incorporated herein by reference. This lactic acid stream could also be sold as final product with purification as needed. The lactic acid could also be reacted to form other products of value such as lactate esters, lactate amides, and acrylic acid.

Distilling off the relatively small amount of lactic acid from the extracting solvent is a particularly attractive approach to lactic acid recovery since the minor component of the solution is being taken overhead. Therefore, an extracting solvent with a lower volatility relative to lactic acid would be preferred.

Alamine 336, a commercially available mixture of tertiary alkylamines with octyl and decyl alkyl groups has a lower volatility than lactic acid. It has been discovered that for a Alamine 336 and aqueous lactic acid mixture at relatively low temperatures (about <65° C.) and certain aqueous free lactic acid concentrations, three liquid phases are in equilibrium; one aqueous free lactic acid concentration is about 2.2 wt %, while the lactic acid concentrations are about 16 wt % and 1.4 wt % for the middle and top organic phases, respectively. The total organic phase or the highly loaded lactic acid-Alamine 336 middle phase can be physically separated from the other phase(s). The lactic acid could then be distilled from the Alamine 336, or the lactic acid extract can be further processed using other methods described in this application to obtain lactic acid products.

It should be noted that at room temperature, if the aqueous free lactic acid concentration at equilibrium is significantly above or below the 2.2 wt %, only a single organic phase will be obtained. Example 2 reports one example of making a three phase system, and how by recontacting the two organic phases with a fresh aqueous lactic acid solution, a single organic phase with a high lactic acid concentration was obtained.

As indicated above, another possible method to obtain the lactic acid from the extracting solvent is to back extract the lactic acid into a liquid phase that is immiscible with the extracting solvent. The second immiscible phase can be water, polar organic compounds, or mixtures of these liquids. It has been found that some polar organic compounds are immiscible with the preferred extracting solvents described above. As the weight fraction of the trialkyl amine and kerosene increases, the probability that a polar organic compound is immiscible with the extracting solvent increases. Polar organic compounds of interest include: methanol; ethanol; lactide; lactic acid oligomers; dimethyl sulfoxide; N,N-dimethyl foramide; N-methyl pyrrolidinone; and sulfolane. In general the polar organic compounds of interest are ones which have a solubility in water greater than 1 g per 10 g of water. The back extraction will preferably be performed at a temperature higher than the initial extraction of lactic acid into the extracting solvent (typically 30° C. to 160° C. or higher, usually at 90° C. to 160° C.). There are exceptions to this and when using an extracting solvent comprising a large proportion alcohol such as hexanol or octanol, it can be favorable to perform the back extraction at a lower temperature than the initial extraction. The composition of the extracting solvent can be changed between the forward extraction of lactic acid and the back extraction. The equipment suitable for the forward extraction as listed above is also appropriate for use in the back extraction.

The back extraction solvent may also have a basic compound to increase the distribution of the lactic acid back into the second immiscible phase. It has been found that the ternary system of triethylamine-lactic acid-trioctylamine at room temperature has two phases. This is somewhat surprising because triethylamine and trioctylamine are miscible. The trioctylamine phase contains little lactic acid if the amount of triethylamine added is slightly more than stoichiometric. The triethylamine-rich phase is nearly a 1:1 molar ratio of lactic acid to triethylamine, which gives a weight percent of lactic acid of 47%. Thus, this system is capable of concentrating the lactic acid during the back extraction. The triethylamine is substantially more volatile than lactic acid and can be distilled to obtain a crude lactic acid product. It is expected that trimethylamine, ammonia, and other amines with a molecular weight of less than 200 would show similar behavior as the triethylamine. Bailey et al. disclose the use of trialkyl tertiary amines in an organic solvent with back extraction into an aqueous phase (with a relatively strong base such as ammonia) in U.S. Pat. No. 4,771,001 incorporated herein by reference).

Back extraction into a mixture of triethylamine in polar solvent with relatively low volatility is an efficient process since the solvent to triethylamine ratio can be carefully controlled. The presence of the solvent allows the viscosity to remain low during the distillation of the amine from the lactic acid and would provide a medium for further reactions of the lactic acid to lactic acid products.

This last recited option of back extracting the lactic acid has been generally described as having a non-polar solvent with a basic extractant, such as a long-chain (18 carbon atoms or more) alkylamine, and using a polar organic solvent as the back extracting phase. Of course, the opposite can be true. The initial extracting solvent can be relatively polar, but still immiscible with water, and the back extraction liquid can be a non-polar solvent with a basic extractant. The fundamental concept is the ability to extract lactic acid from an aqueous solution with an extracting solvent and back extracting the lactic acid into a second liquid. In some cases that liquid will be water, but it can also be an organic liquid that is appropriate for efficient separation of the lactic acid or to make and separate lactic acid products.

When back extracting the lactic acid into a second polar liquid phase, there will be a residual amount of the extracting solvent components in the lactic acid rich back extraction phase. If desired, the residual extracting solvent can be decreased by contacting the back extraction phase with a non-polar solvent such as IsoPar K. This extra purification is shown in Example 3.

Another option for separating the lactic acid out of the extract is the use of a membrane-process. In this case, the lactic acid passes through the membrane to a phase different in composition than the extracting solvent. One possible case is when the extracting solvent contains a long-chain alkylamine in a non-polar solvent. On the other side of the membrane is a volatile base, such as trimethylamine, in the same non-polar solvent. The membrane is an anion exchange membrane which doesn't allow cations, such as trimethylammonium, to pass. The lactic acid passes through the membrane to form a lactate:trimethylammonium complex. The volatile base is then removed by distillation and lactic acid products can be made and separated in the non-polar mixture. In general, the use of the membrane allows the conduct of phase separation between two otherwise miscible liquids.

As indicated previously, the formation of the alkyl lactate ester can be a condensation reaction between the lactic acid and a hydroxyl group on another molecule. This other molecule could be another lactic acid molecule or any other molecule that has a hydroxyl group. Possibilities include methanol, ethanol, butanol, octanol, dodecanol, 2-ethyl hexanol, and 1,4-butane diol. The condensation reaction is driven towards the production of the ester by the removal of the ester and/or water from the reaction mixture. The condensation reaction can be performed in the extracting solvent or the polar liquid that is used for the back extraction. The separation of the lactate ester can be performed by evaporation or extraction.

The alkyl lactate ester could also be formed by a transesterification reaction between the lactic acid carboxylic acid group and an ester. The by-product of a transesterification reaction is an acid, and the reaction is driven forward to the production of the lactate ester by the separation of the acid and/or the lactate ester from the reaction mixture. The use of formate esters, acetate esters, or other esters which have a corresponding acid that is more volatile than lactic acid and the formed lactate ester are good choices because the volatile acid can be evaporated out of the reaction mixture to drive the reaction to completion. The lactate ester can then be evaporated or back extracted into an extracting solvent immiscible phase.

An ester with a corresponding acid that has a lower volatility than lactate ester formed could be used. The reaction is driven to completion by the separation of the lactate ester from the reaction mixture. Suitable esters for this type of process would be methyl ocanoate, dimethyl succinate, and ethyl decanoate. The advantage of this system is that the lactate ester product is immediately removed from the reaction mixture. The disadvantage is that the by-product acid must be efficiently regenerated back to the desired ester.

In the transesterification processes described above, the initial ester was chosen due to the relative volatility of the corresponding acid. This was because evaporation was chosen as the method to remove the products of the transesterification reaction. If back extraction into a phase that is immiscible with the extracting solvent is used to separate the products of the transesterification reaction, the initial ester would be chosen based on the selectivity of the immiscible phase for the corresponding acid or lactate ester. For instance, if an immiscible phase was found to select for succinic acid over lactic acid, butyl lactate, butyl succinate, and dibutyl succinate, the condensation reaction could be driven to butyl lactate by extracting away the succinic acid.

The alcohol or initial ester can be part of the extracting solvent or added to the lactic acid extract after it is separated from the aqueous phase. As mentioned, the removal of the products of the condensation reaction is important to drive the reaction towards formation of the lactate esters. This removal can be simultaneously or sequentially. Reactive distillation would be suitable for the simultaneous removal of one of the reaction products. A sequential separation process may require a direction (recycle)of material back to the condensation reactor for efficient operation.

The lactate ester can be further purified if required, especially if the lactate ester is the final product of interest. Once an appropriate lactate ester stream is obtained, polylactic acid can be obtained by the following method. Any free water in the system would be separated, and the stream would be heated, possibly under subatmospheric pressure. The lactate ester's corresponding alcohol would be evaporated from the reaction mixture to drive the transesterification reaction. For instance, a methyl lactate stream would give off methanol and a lactoyl methyl lactate. As the methanol is evaporated off, the molecular weight of the methyl capped lactic acid oligomer increases. This stream would then be fed to a lactide formation reactor where a catalyst is added. Lactide, the cyclic ester of lactic acid, would then form and be used to form polylactic acid. Processes to make lactide from alkyl lactate esters have been disclosed by Gruber, et al. in U.S. Pat. Nos. 5,247,059 and 5,274,073, each of which is incorporated herein by reference.

Lactic acid oligomers are also lactic acid products of interest that could be used to make polylactic acid. Earlier, a preferred process was described for taking a lactic acid-rich extract and make lactic acid oligomers. The oligomer formation is performed in the presence of the extracting solvent, with the reaction being driven by the removal of water. The preferred process is to remove water by evaporation, typically under subatmospheric pressures. There are other methods to remove water that are suitable such as adsorption on molecular sieves or silica, reaction with an anhydrous salt to form a hydrated salt, and passing water preferentially through a membrane, such a pervaporation. Generation of lactic acid oligomers is generally discussed in U.S. Pat. No. 4,142,023.

If the extracting solvent is relatively volatile, the extracting solvent could also be removed by evaporation leaving a concentrated lactide acid oligomer stream. A preferred process would have the volatile extracting solvent forming an azeotrope with water, thus aiding in the water removal step.

If the extracting solvent cannot be easily evaporated, other methods to separate the lactic acid oligomers from the extracting solvent are used. These methods are suitable when the extracting solvent includes a high molecular weight trialkylamine, such as tridodecyl amine, or high molecular weight oxygenated phosphorus compound, such as tributyl phosphine and trioctyl phosphine oxide. It has been found that the prepolymer can be substantially separated from the extracting solvent by causing the creation of two immiscible phases.

It has been found that when Alamine 336 is used as the extracting solvent, a significant amount of the trialkylamine can be separated from the lactic acid oligomers with little additional effort. The Alamine 336-lactic acid extract is subjected to conditions that cause the condensation of lactic acid to lactic acid oligomers. It has been found that upon cooling this mixture, two immiscible phases are obtained. One of the phases is Alamine 336 enriched, and the other is lactic acid oligomer enriched. It was found that the lactic acid oligomer enriched phase had an Alamine 336 concentration about equal to a 1:1 molar ratio of amine to lactic acid oligomer. Therefore, as the average molecular weight of the oligomers increases, the average amount of residual Alamine 336 in the oligomer-rich phase will decrease.

There are other ways to force the creation of a second liquid phase. Acid or base displacement are suitable methods to use when the extracting solvent contains a high molecular weight tertiary amine. The oligomer still has a carboxylic acid end that can strongly interact with an amine group. If another acid is added to the system and the amine selectively prefers this other acid, this acid will interact with the amine and the oligomer is free to partition in to a separate phase. The required amount of said other acid is equivalent to that of the oligomer. Thus, the higher the molecular weight of the oligomer, the lower amount of the other acid is required. Alternatively, another base could be added to the system and the carboxylic acid end of the oligomer could selectively prefer this other base. The amine could then form a second liquid phase. The displacing acid or displacing base need to be separated from the amine phase or oligomer phase, respectively, possibly via distillation or ion exchange. The displacing acid or base may be added in a solution and the solvent associated with the displacing species may need to be separated as well.

If the lactide formation is conducted, and it is performed at temperatures between about 150° C. and 250° C. and pressures from about 2 mm Hg to 100 mm Hg, the lactide produced will evaporate. This stream of crude lactide may need to be further purified to meet the purity requirements for making quality poly lactic acid.

If a stream from the lactide formation reactor is cooled, the stream may produce a new solid phase. Lactide with a chiral purity of greater than 95% has a melting point of about 96° C. Therefore, lactide can be crystallized from the extracting solvent provided the concentration of lactide exceeds the solubility of the lactide in that solvent. If the solubility of the lactide is not exceeded, the addition of another liquid, an anti-solvent, to the lactide stream may decrease the solubility of the lactide such that the lactide crystallizes. Filtration of the slurry provides a crude lactide stream that can be used for polymer formation.

Another method for lactide isolation, from the lactide formation reactor, is to cause the lactide to phase split from the extracting solvent. This phase split could be caused by changing the temperature of a stream or adding liquid solutions to the stream leaving the lactide formation reactor. It has been found that lactide is immiscible with Alamine 336 and mixtures of Alamine 336 and IsoPar K, an aliphatic solvent from Exxon. Therefore, lactide could be concentrated and further processed to poly lactic acid if Alamine 336 is used as the extracting solvent.

In some processes, it may be desirable to convert the lactate salt, from the fermentation, to another salt, to facilitate the separation, for example, the calcium salt could be converted to the sodium salt.

VII. Some Specific Processing Schemes

The techniques described below in connection with the Figures are often presented with respect to the process system involving processing of a fermentation broth by removal, from the aqueous phase, of the lactic acid: Downstream processing steps conducted with respect to the lactic acid component are sometimes described. Of course it is not necessary that the downstream processing of the lactic acid/lactate mixture be conducted of a fermentation broth directly, i.e. without some prior modification of the broth other than merely filtration. For example, pH adjustments to the broth for example to a pH of about 2.0, can be conducted. Further, the downstream processing of lactic acid fraction can be conducted after a previous step of lactate removal from the broth or mixture, if desired.

It is also noted that the techniques presented in the Figures can be applied in both continuous processes and batch processes, as desired. As a result, the techniques indicated in the figures are well adapted for commercial implementation.

A. FIG. 1; Extraction of Lactic Acid, Lactate Salt and Nutrients Recycled,(Optional) Extract Regenerated, Lactic Acid Concentrated by Distillation.

FIG. 1 is a schematic representation of a preferred lactic acid recovery process in which the lactic acid solution is formed by fermentation. Referring to FIG. 1, the fermentor is indicated generally at 1. Via line 2, the fermentation broth is removed from the fermentor 1. The fermentation broth is passed through a filter unit 3, with removed solids (for example, cell material) shown taken off of line 4 and the clarified or filtered liquid transferred into an extraction process or extraction unit 6. The filter unit 3 may comprise a simple physical filter, or it may include adsorptive materials such as activated carbon and/or physical ion exchange media. Preferably, an approach is chosen so that sterilization of the material before recycling is not required. (Of course the cells, in many instances, can be directed back into the fermentor 1, if desired.)

More specifically, the liquid in line 5, comprising an aqueous solution of lactic acid and lactate salt, is directed into an extraction unit 6 such as an agitated column, perforated plate column or a series of mixer settlers. Two or more such units can be used in series, for a multi-step extraction process. The extractant is shown fed into the system via line 7, with the lactic acid carrying extractant phase removed via line 8. The raffinate or residual aqueous phase (lactic acid depleted), containing the lactate salt and any residual nutrients is shown removed via line 10 and directed into a pretreatment system 11, for return to the fermentation broth via line 12. The pretreatment system 11 may be, for example, a solvent back wash to remove any level of residual extract which may be toxic to the organisms in the fermentor, or to remove some other undesired impurities to avoid impurity build-up in the fermentor due to recycling.

The extractant phase, containing the lactic acid, is directed in a distillation system 13. The lactic acid products are distilled via line 15. The resulting lactic acid product comprises lactic acid and condensation products (oligomers) of lactic acid (depending on the extent of concentration in distillation system 13). It can be used to form lactide and polymer. The extracting solvent is removed via line 14 and is shown recycled in the extraction.

The schematic of FIG. 1, then, is particularly well suited for use in systems wherein the lactic acid is removed from the fermentation broth by extraction, and recovery of the lactic acid results from distillation of the lactic acid away from the extractant. The schematic of FIG. 1 is suitable, for example, for application wherein the extractant phase comprises a mixture of tertiary amines and alkanes, such as Alamine 336, and kerosene.

Specific preferred conditions for the extraction would involve contacting the aqueous lactic acid solution and extracting solvent at a temperature between 30° C. and 50° C. The aqueous to organic phase ratio is preferably between 0.1 and 10, and more preferred is between 0.2 and 5.

Of course a process similar to FIG. 1 could be practiced on a variety of solutions other than simply fermentation broths. The material in line 5 could be modified broth (acidified for example) or it could be from a source other than fermentation.

Alternatively, if the extracting solvent is more volatile than lactic acid, the same flowsheet as FIG. 1 is appropriate. However, the extracting solvent would be distilled from the lactic acid products).

Figure 2:
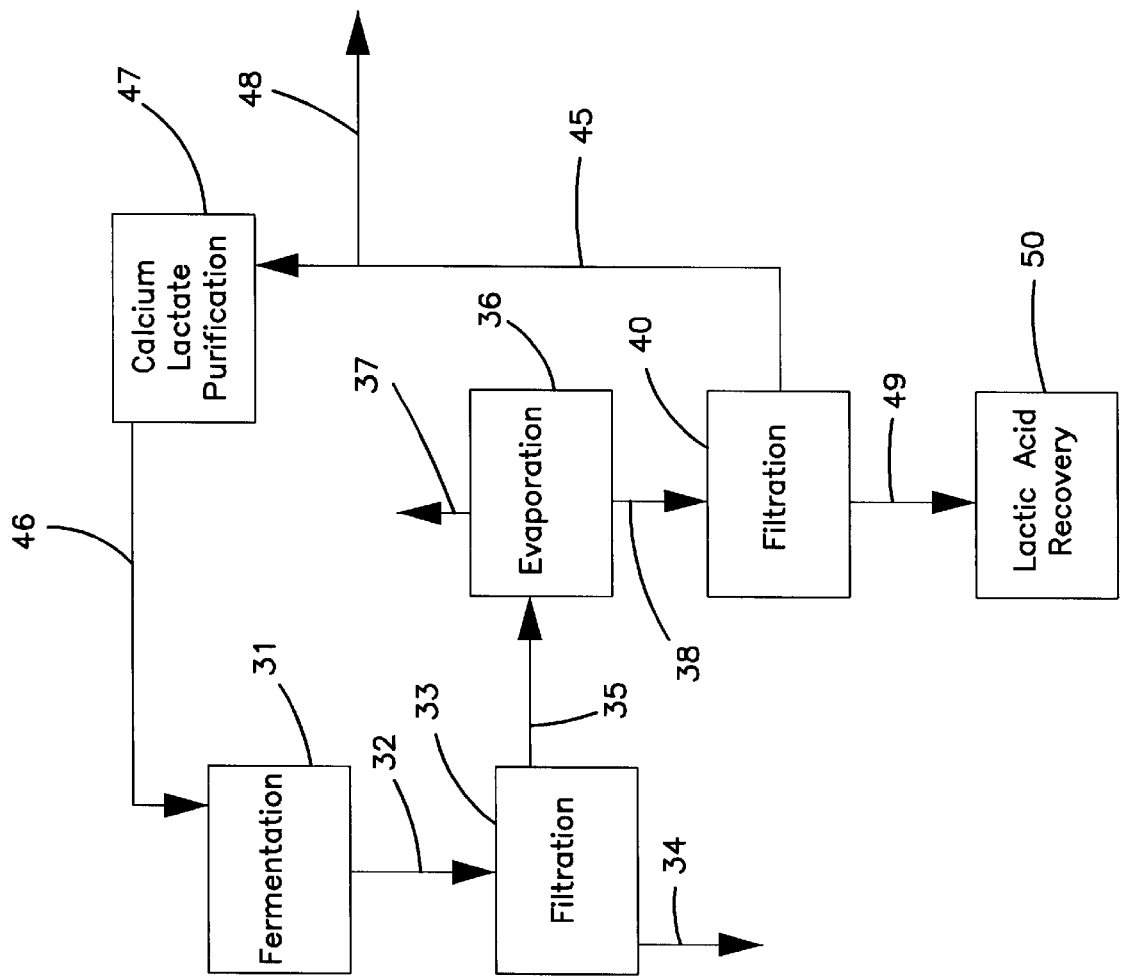
FIG. 2 is an alternate process flow diagram to the one shown in FIG. 1.

B. FIG. 2; Lactate Crystallization from Broth, Recycle of Lactate Salt to Fermentation; Recovery of Acid from Salt Depleted Broth.

Attention is now directed to the schematic of FIG. 2. In this alternative approach, a lactate salt of relatively low solubility, e.g. calcium lactate, is precipitated from the mixture, and the lactic acid is recovered from the mother liquid. Referring to FIG. 2, the fermentor is indicated generally at 31. The fermentation broth is shown removed via line 32 to be directed through filter or clarifier 33. The solids from the clarifier are shown removed via line 34. The clarified broth is then directed via line 35 into evaporation unit 36. (Of course the material in line 35 could be modified broth or a mixture from some other source.) During evaporation, concentration and crystallization of the lactate salt contained within the broth will occur. Water from the evaporation is shown drawn off via line 37. Physical separation of the mother liquor from the crystallized material is shown by directing the result of the evaporation, line 38, through filter 40. The solids recovered from the filter 40, comprising crystallized lactate, are shown directed via line 45 into a purification unit and eventually (if desired) recycled to the fermentation via line 46 (with optional purification at station 47 if desired). Of course, alternatively they may be directed into other processing (line 48). A combination of the two may be preferred in some circumstances.

The mother liquor from the filtration is shown directed via line 49 into lactic acid recovery 50. The lactic acid recovery step can be any of the variety of steps characterized above.

In general, the schematic of FIG. 2 will be particularly useful when the lactate salt is calcium lactate due to low solubility of calcium lactate in aqueous solutions. It is noted that the calcium lactate recovered will make an excellent buffer or pH adjuster for the fermentation broth.

Figure 3:
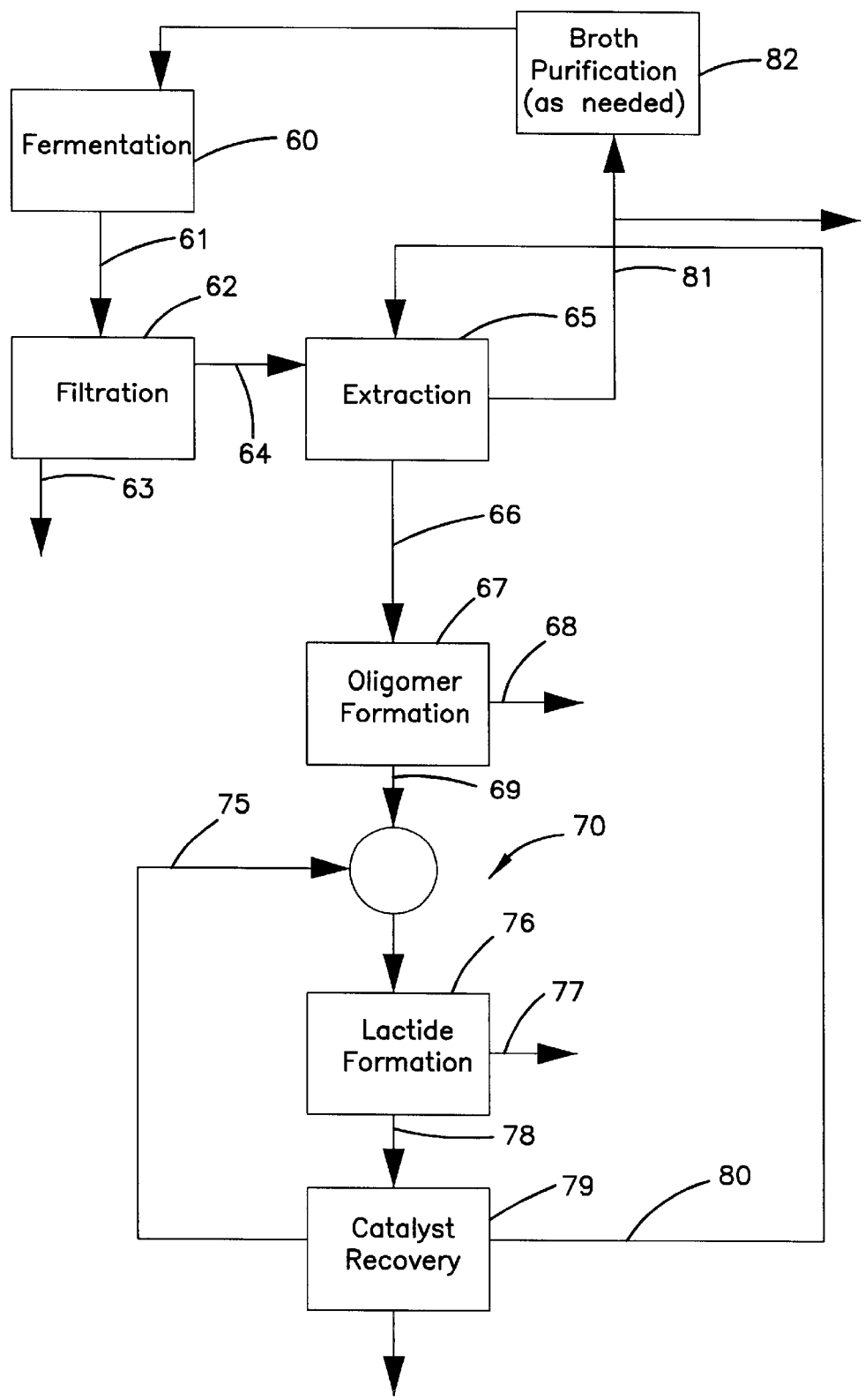
FIG. 3 is an alternate process flow diagram to the ones shown in FIGS. 1 and 2.

C. FIG. 3; Extraction of Lactic Acid, Formation of Oligomer and Lactide in Extracting Solvent.

Attention is now directed to the schematic of FIG. 3. This approach will be particularly useful when the intent is to directly produce, as a "lactic product", lactide and/or oligomer of lactic acid, without previous isolation of lactic acid, and, preferably, without a step of back extraction.

Referring to FIG. 3, the fermentor is indicated generally at 60. Fermentation broth is shown removed from the fermentor 60 via line 61, for direction into clarifier filtration unit 62. Solids from the filtration unit are shown removed via line 63. The clarified fermentation broth, or other mixture such as modified broth, containing lactic acid and lactate salt, is shown directed into an extraction unit via line 64. The extraction unit is indicated generally at 65, and may comprise more than one stage of extraction. These stages may be generally as described above in connection with FIG. 1. Alternatively, the salt is separated first as in FIG. 2 and the mother liquor is extracted. The extractant phase is shown removed via line 66, and is directed into unit 67 for oligomer formation. Unit 67 may comprise, for example, a multi-stage evaporating unit, from which water and other volatiles are shown driven off via line 68 as the extractant is concentrated and the lactic acid condenses to form oligomer.

The resulting lactic product phase (oligomer) is shown removed from the multi-stage evaporator via line 69, and is directed into reactor stage 70. In the reactor stage 70, catalysts may be added, for example via line 75, to facilitate lactide formation. The lactide formation step, indicated generally at 76, results in generation of crude lactide, shown drawn off via line 77, and reactor bottoms shown withdrawn via line 78, for catalyst recovery or other treatment 79. The catalyst, of course, can be recycled, if desired, via line 75.

The extracting solvent is shown removed from the lactide formation phase via line 80, for recycling into the extraction.

Still referring to FIG. 3, in the extraction step, the aqueous phase is shown withdrawn via line 81 for optional recycling as desired back to the fermentation broth. Purification of this, if needed, is shown indicated at equipment 82. Such purification may be desired, for example, if the extractant is one which is toxic to the microorganisms of the fermentation broth. Approaches to removal of such materials were discussed above.

From a review of the above, and FIG. 3, it should be apparent that with the techniques described "direct" oligomer formation can be conducted without a step of back extraction or otherwise separating the lactic acid from the extraction; and, they direct lactide formation, from the oligomer, can be conducted even if residual extractant is present in the oligomer. Thus, with the techniques presented, highly efficient processes can be developed.

Figure 4:
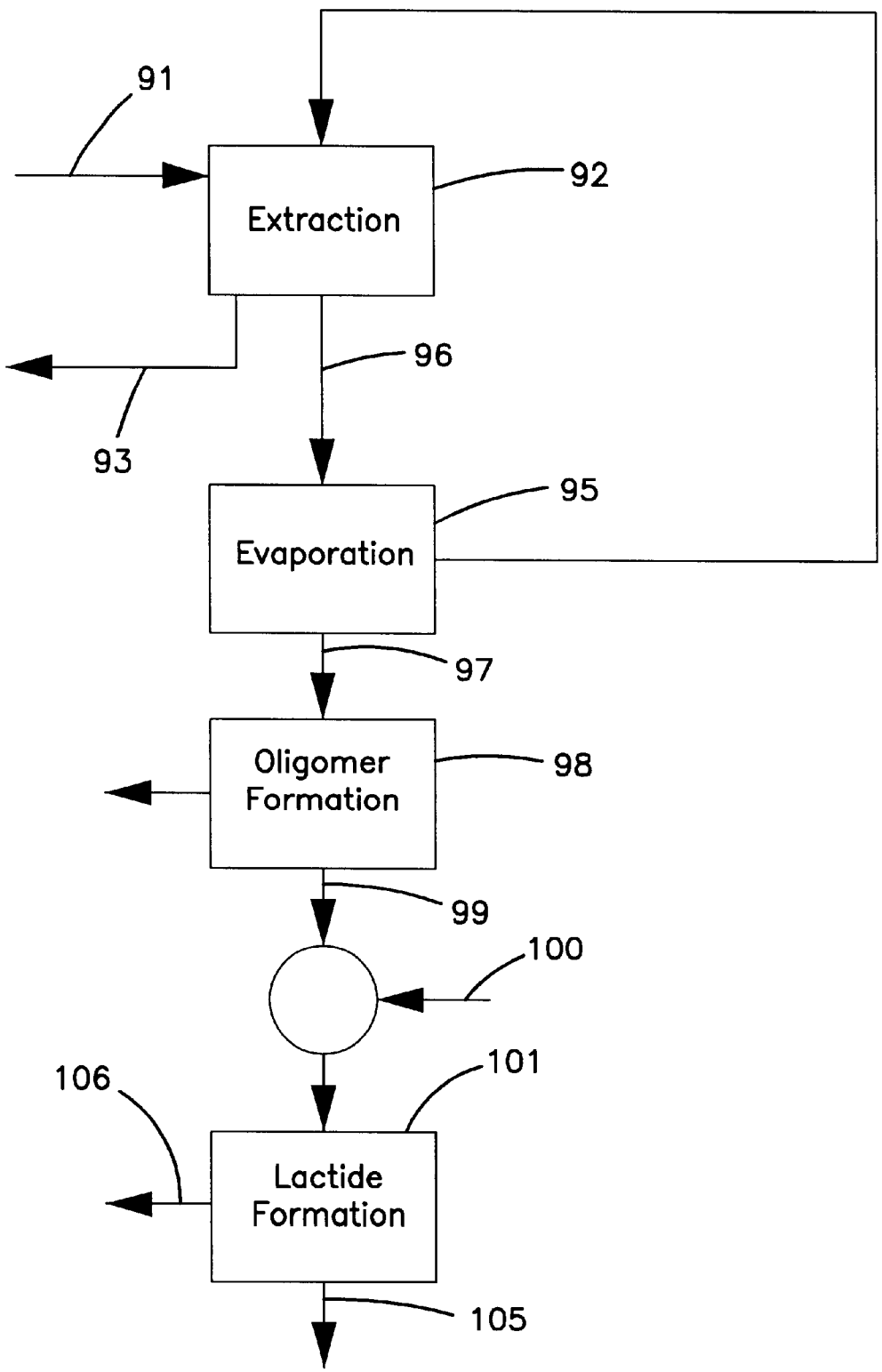
FIG. 4 is an alternate process flow diagram to the ones shown in FIGS. 1–3.

D. FIG. 4; Extraction of Lactic Acid; Distillation of Solvents; Oligomer Lactide Formation by Condensation.

Attention is now directed to FIG. 4. In FIG. 4, lactic acid and lactate aqueous feed from a fermentor, typically following clarification, is shown in line 91. The feed (or other mixture) is directed into an extraction system 92. As with previous arrangements described, the extraction system 92 of FIG. 4 may comprise multiple stages, each of which may comprise extraction equipment as previously characterized. The aqueous raffinate (lactic acid depleted) is shown removed from the system via line 93. The raffinate will include the lactate salt, and may be treated for recycling to the fermentation broth via techniques previously described. The extractant phase is shown directed to an evaporator 95, via line 96. In the evaporator, the extracting solvent is removed under distillation conditions, typically low pressure. For example, hexanol and other alkanols with 4 to 7 carbons, and methyl isobutyl ketone or other ketones with 5 to 9 carbons, can be used to extract lactic acid from an aqueous solution. The alkanols (and/or ketones) can then be distilled from the lactic acid at temperatures below about 120° C. Keeping the temperature low is important to reduce the condensation reaction with lactic acid and the alkanol.

The nonvolatiles from the evaporator are shown directed via line 97 into a system 98 for oligomer formation. Within the system 98, generally a lactic acid condensation reaction is facilitated by concentration and removal of water. The oligomer is removed from the reactor 98 via line 99. Catalyst is added, via line 100, and lactide formation is generated, as indicated at system 101. The crude lactide stream is then removed from the re actor of line 105, with the catalyst purge shown removed via line 106. The lactide formation step may be conducted as generally described in U.S. Pat. Nos.: 5,142,023; 5,247,058; 5,258,488; and 5,357,035, incorporated herein by reference.

Figure 5:
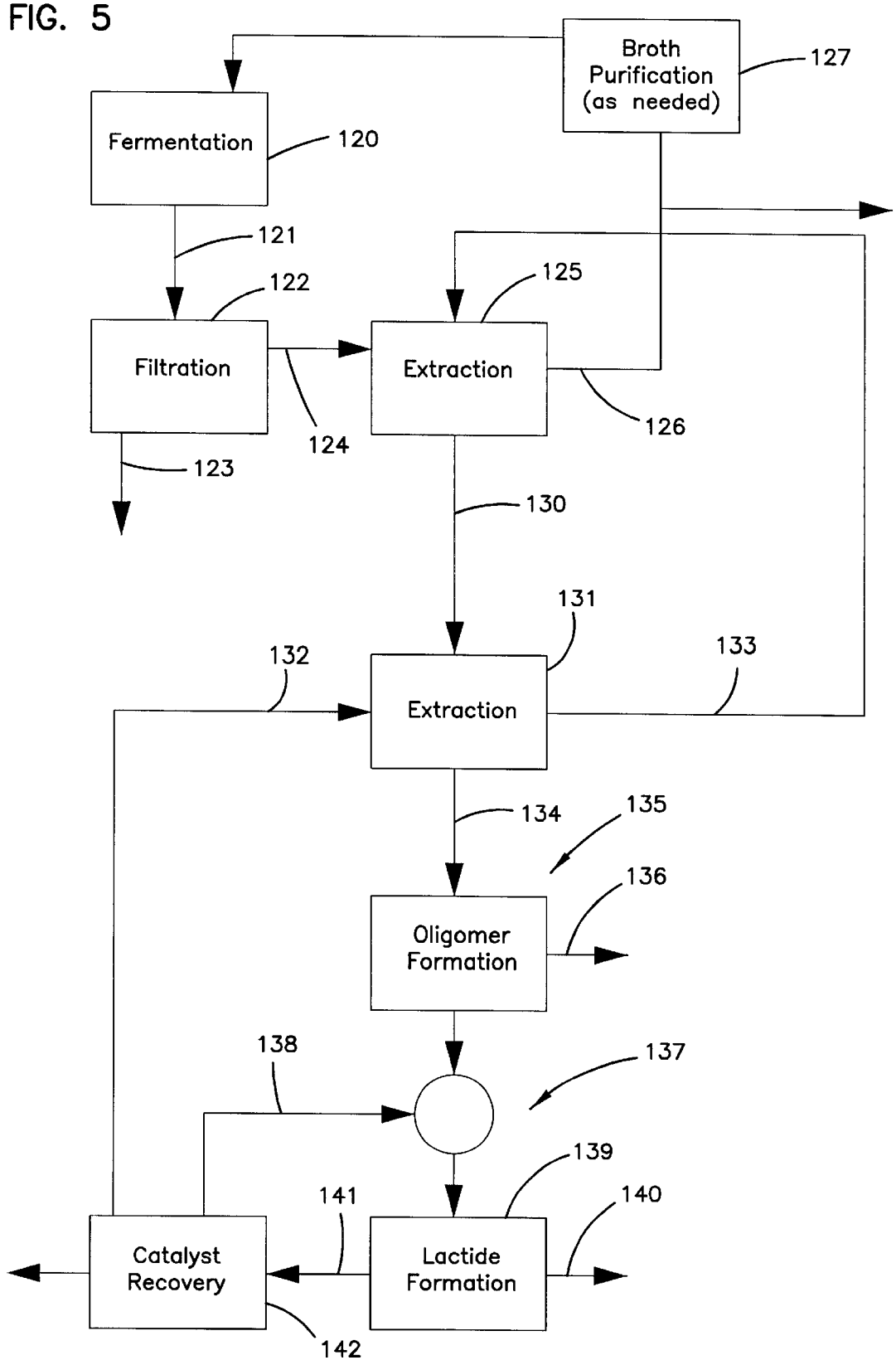
FIG. 5 is an alternate process flow diagram to the ones shown in FIGS. 1–3.

E. FIG. 5; Extraction of Lactic Acid; Raffinate Recycle; Back Extraction of Lactic Acid into Second Polar Phase; Formation of Oligomer and Lactide in Second Polar Phase;

Attention is now directed to FIG. 5. In FIG. 5, the fermentor is indicated generally at 120. Fermentation broth is shown removed from the fermentor 120 via line 121, for direction through clarifier filter 122. Solids are removed from the filter via line 123. The aqueous phase, containing lactic acid and lactate salt, is shown directed into an extractor system 125 via line 124. (Of course this phase could also be modified broth or some other mixture.) The aqueous phase (raffinate) is removed via line 126 for direction through a purifier 127, if desired, and eventual recycling into the fermentor 120.

The extractant phase is shown removed from the extractant system 125, via line 130. The extractant phase is directed into a second extractant step or system 131. (Of course, the same physical extraction equipment can be used for both extractions.) A second polar liquid is shown directed into the extractor 131 via line 132. The lactic acid will be preferentially extracted into the second polar liquid, with the original extracting solvent from extractor 125 shown removed via line 133, for recycling. The second polar liquid, containing the lactic acid therein, is shown withdrawn from the extractant system via line 134, for direction into a system 135 for oligomer formation. This would be conducted as previously described, with condensation occurring as a result of water being driven off via line 136. The oligomer is then shown directed into a reactor system 137, for mixing with a catalyst directed into via line 138. Lactide formation is indicated generally at 139, with crude lactide removed via line 140, and the reactor purge, containing a catalyst, being shown directed via line 141 the catalyst recovery 142. This recovered polar liquid can then be cycled back into the system as shown by line 132.

Figure 6:
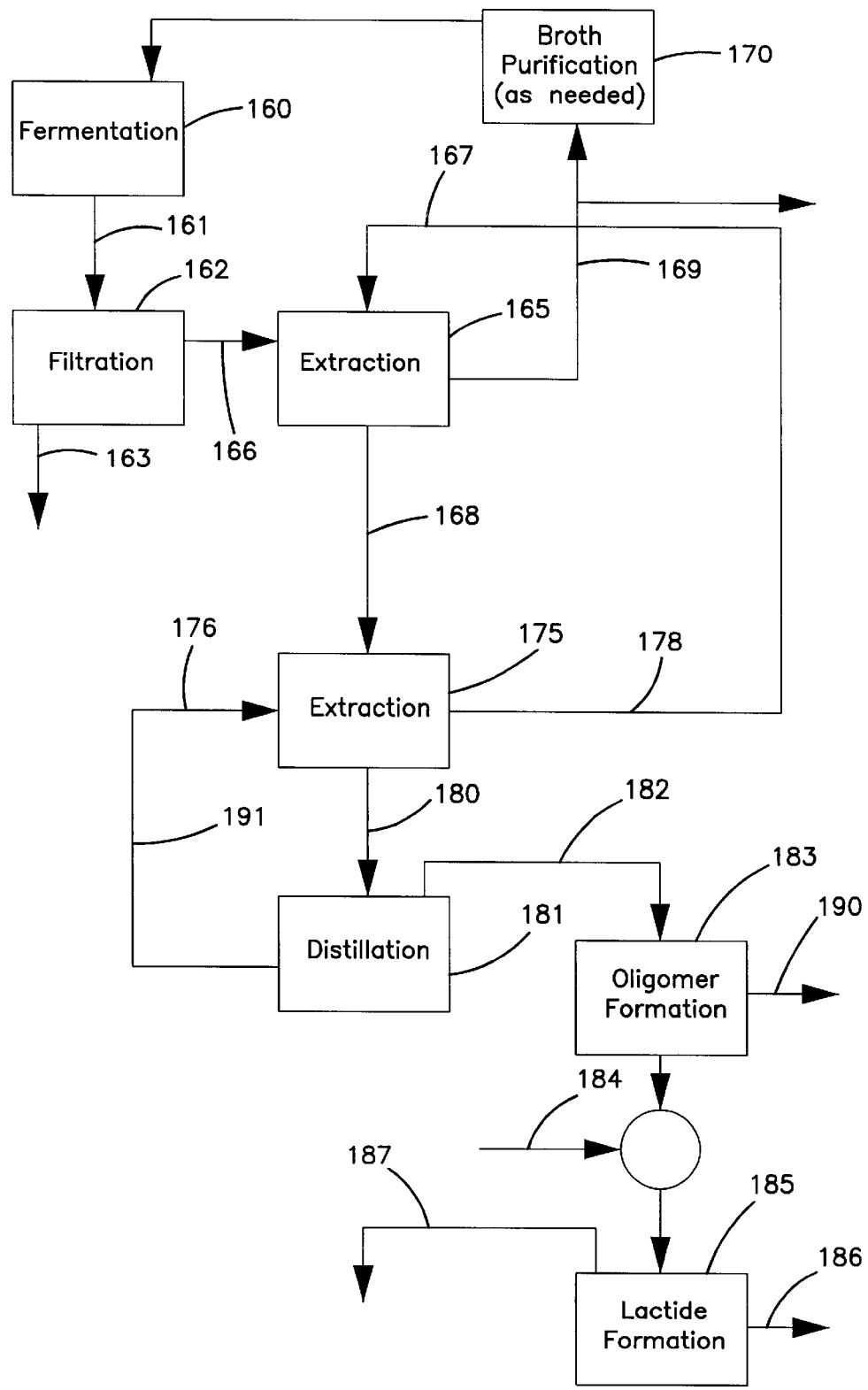
FIG. 6 is an alternate process flow diagram to the ones shown in FIGS. 1–5.

F. FIG. 6; Extraction of Lactic Acid: Raffinate Recycle; Back Extraction into the Second Polar Phase; Lactic Acid Purified by Distillation; Follow-Up (Optional) Oligomer and Lactide Formation.

Attention is now directed to FIG. 6. A fermentor is indicated generally at 160. The fermentation broth, containing lactic acid and lactate salt, is shown withdrawn via line 161 and is directed through filter 162. Solids are shown removed via line 163. The mixture of lactate salt and lactic acid is shown directed into an extractor system 165 via line 166. (Of course this mixture could also be modified broth or a mixture other than fermentation broth.) The extractant is shown fed in via line 167, with the extractant phase withdrawn via line 168, and the residual aqueous phase, containing the lactate salt, removed via line 169. The residual lactate phase is then directed for broth purification, if desired, into purifier 170 and eventually for recycle into fermentor 160. The extractant phase is shown directed via line 168 into back extractor unit 175. The second polar liquid is shown directed into the back extractor system 175 via line 176, with the original extracting solvent (from extraction at 165) shown drawn off via line 178 for recycling into the first extracting system 165; and, with the second polar liquid, containing the lactic acid, shown removed via line 180 and directed in distillation system 181. Within the distillation system 181, either the lactic acid will be distilled from the second polar liquid, or the second polar liquid will be distilled from the lactic acid, depending upon the relative volatilities. The separated lactic acid is shown directed via line 182 into downstream oligomer formation at 183, with follow-up catalyst addition at 184 and lactide formation at 185. Crude lactide is shown removed via line 186, with the lactide formation purge shown at 187. At line 190, water is shown expelled during the oligomer formation. The second polar liquid is shown removed from the distillation step 181 via line 191. The second polar liquid of course, can be recycled into the second extraction system 175.

Figure 7:
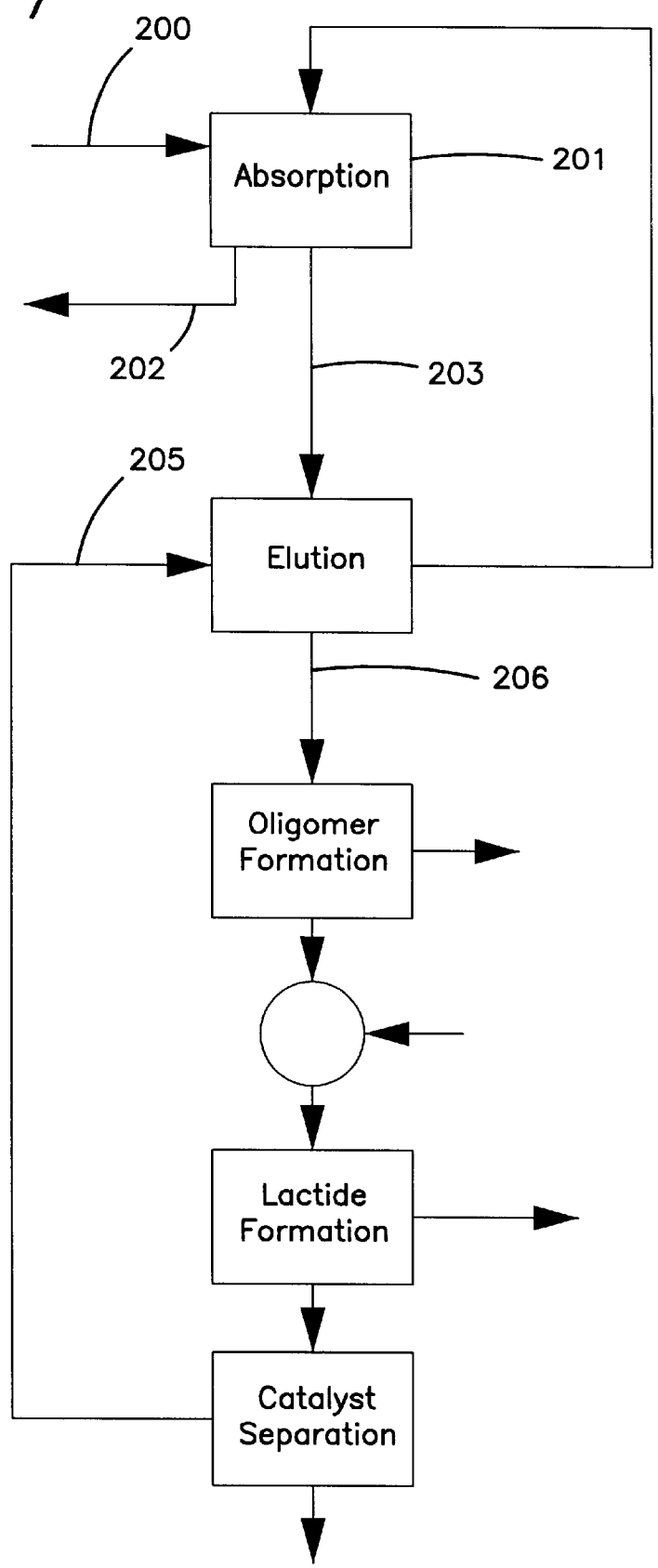
FIG. 7 is an alternate process flow diagram to the ones shown in FIGS. 1–6.

G. FIG. 7; Adsorption of Lactic Acid; Elution by Liquid; Optional Oligomer and Lactide Formation.

Attention is now directed to FIG. 7. A feed of fermentation broth (or other lactic acid/lactate salt mixture) is shown at line 200. This feed is shown directed into a system 201 containing solid adsorbent lactic acid. In this system, the aqueous feed is contacted with the solid adsorbent, with the depleted aqueous phase shown removed via line 202. For this system, the solid adsorbent would be an adsorbent preferentially adsorbing lactic acid verses lactate. Weak anion exchangers would be preferred for this, as characterized above.

The solid adsorbent is shown removed from the contacting step or system 201, via line 230.

The solid adsorbent is shown treated with an eluting liquid introduced via line 205. The eluting liquid would remove the lactic acid from the solid adsorbent. The eluting liquid is shown removed via line 206. Of course, the eluting liquid can be directed into downstream oligomer formation steps and/or lactide formation steps (as indicated), or other processing for isolation of the recovered lactic acid, as desired. After the step of eluting, the solid adsorbent can be appropriately prepared for use (via recycling) in still further in steps of adsorption.

Figure 8:
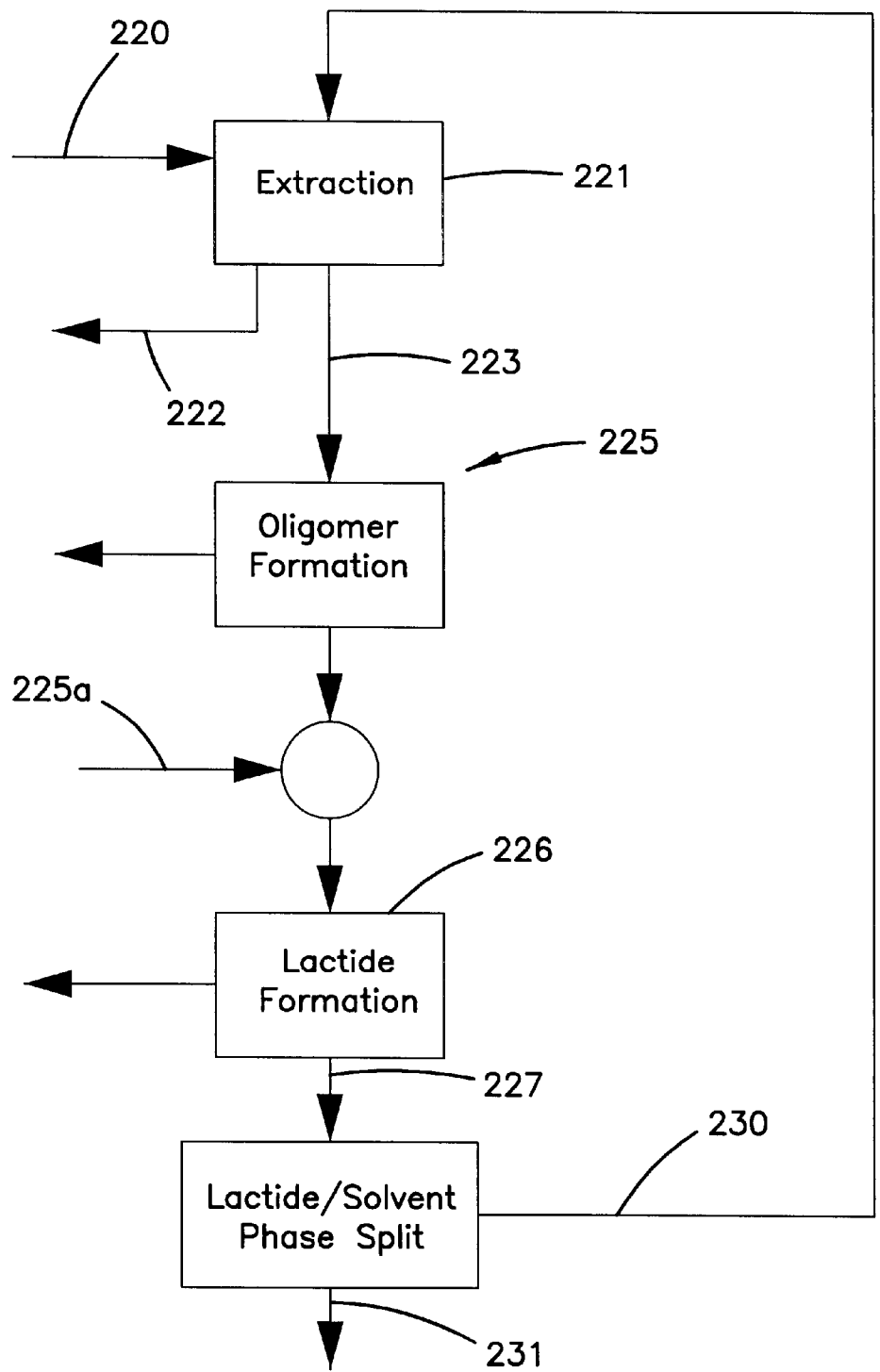
FIG. 8 is an alternate process flow diagram to the ones shown in FIGS. 1–7.

H. FIG. 8; Extraction of Lactic Acid; Oligomer and Lactide Formation in Extracting Solvents; Lactide Purification of Phase Split.

Attention is now directed to FIG. 8. The fermentation broth feed (or other mixture), containing lactic acid and lactate, is shown directed into an extraction system 221 via line 220. The aqueous phase (raffinate) containing the lactate salt is shown removed via line 222. The extractant phase, containing the extracted lactic acid, is shown removed via line 223. It is then directed into processing for oligomer formation at 225 with catalyst addition 225a, and eventually lactide formation at 226, using techniques previously described. The lactide is shown removed from the lactide formation step via line 227 and is directed into a lactide/solvent phase split. This could, for example, be a system in which the reaction mixture is cooled to a temperature between about 70° C. and 150° C. causing the lactide to spontaneously phase split with the extracting solvent. At this point, the extracting solvent is removed from the lactide, and is recycled via line 230. During oligomer formation, water resulting from the condensation is shown removed via line 231. The oligomer can then be directed to lactide formation. Herein, such a process will sometimes be referred to as "direct" formation of lactide from the non-aqueous extractant phase because there was no intervening back extraction step for the lactic acid from the extractant phase. Rather, the lactic acid was condensed and then reacted to lactide. Such "direct" formation can be practices with a variety of the approaches described herein.

Figure 9:
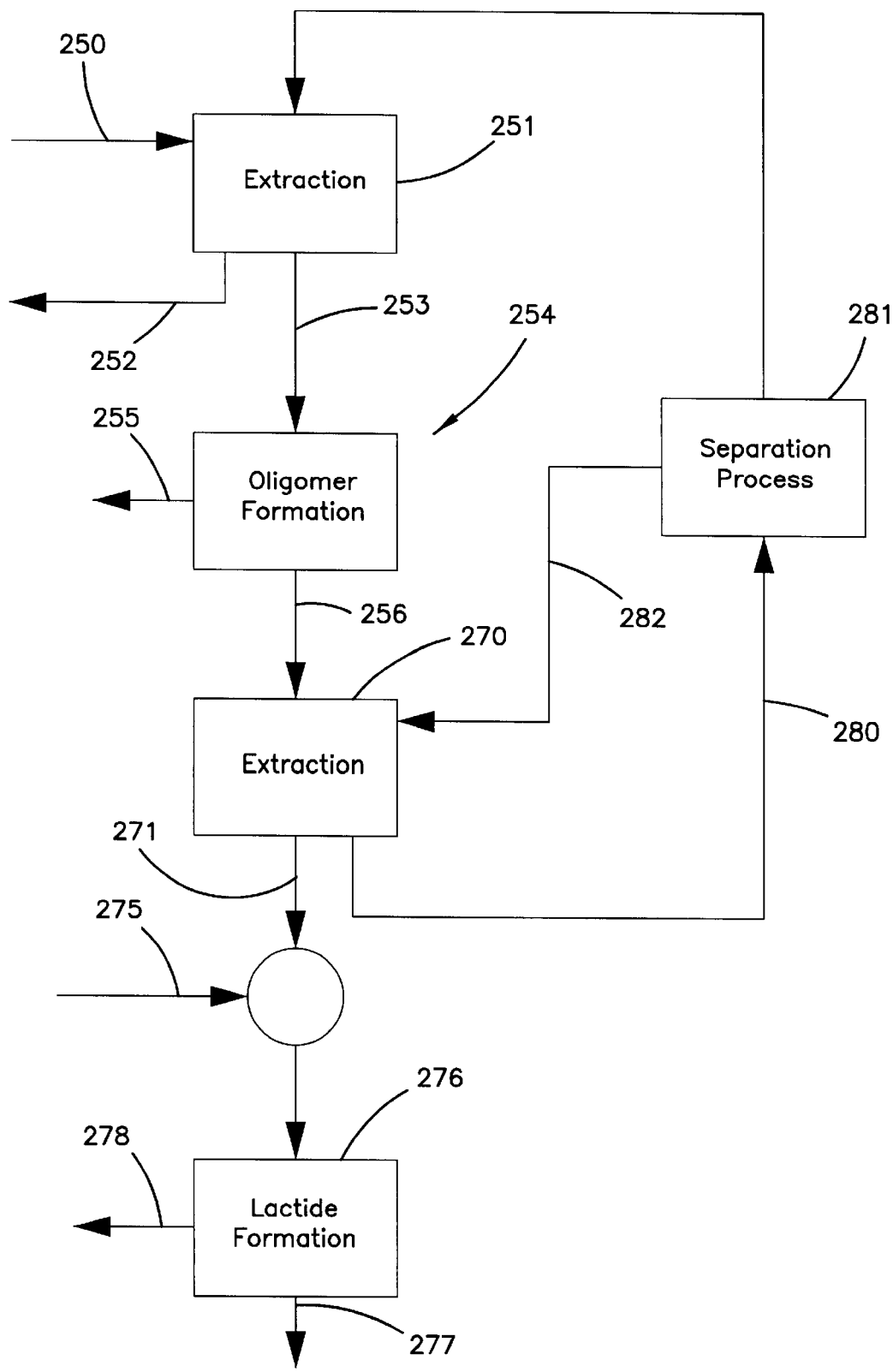
FIG. 9 is an alternate process flow diagram to the ones shown in FIGS. 1–8.

I. FIG. 9; Extraction of Lactic Acid; Oligomer Formation and Extracting Solvents; Oligomer Purification by Phase Split; Lactide Formation from Oligomer.

Attention is now directed to the schematic of FIG. 9. Feed of lactic acid/lactate solution from a fermentor or other source is shown at line 250 being directed into an extractor unit 251. The aqueous raffinate, containing the lactate salt, is shown removed from the extractor unit 251 via line 252. The extracting solvent containing lactic acid therein is shown removed via line 253 and is directed into an oligomer formation step as previously described at 254. Water is expelled from the oligomer formation via line 255, with the oligomer directed into following processing via line 256. In phase splitting/extraction unit 270, the lactic acid oligomer and extracting solvent mixture is cooled to about 0° C. to 60° C. With relatively non-polar extracting solvents, the lactic acid oligomers will spontaneously phase split and nothing needs to be added via line 282. Relatively polar extracting solvent may need to have a phase splitting compound, such as those described in Example 18, added to generate two phases. The lactic acid-oligomer rich phase is removed via 271 and treated by addition of catalyst at 275 for formation of lactide at reactor 276. Crude lactide stream is shown removed via line 277, with the reactor pure, containing the catalyst, removed at line 278. In line 280, the phase splitting compound, if any, is removed from the extracting solvent via distillation or ion exchange at 281. The regenerated extracting solvent is recycled back to the extractor 251.

Figure 10:
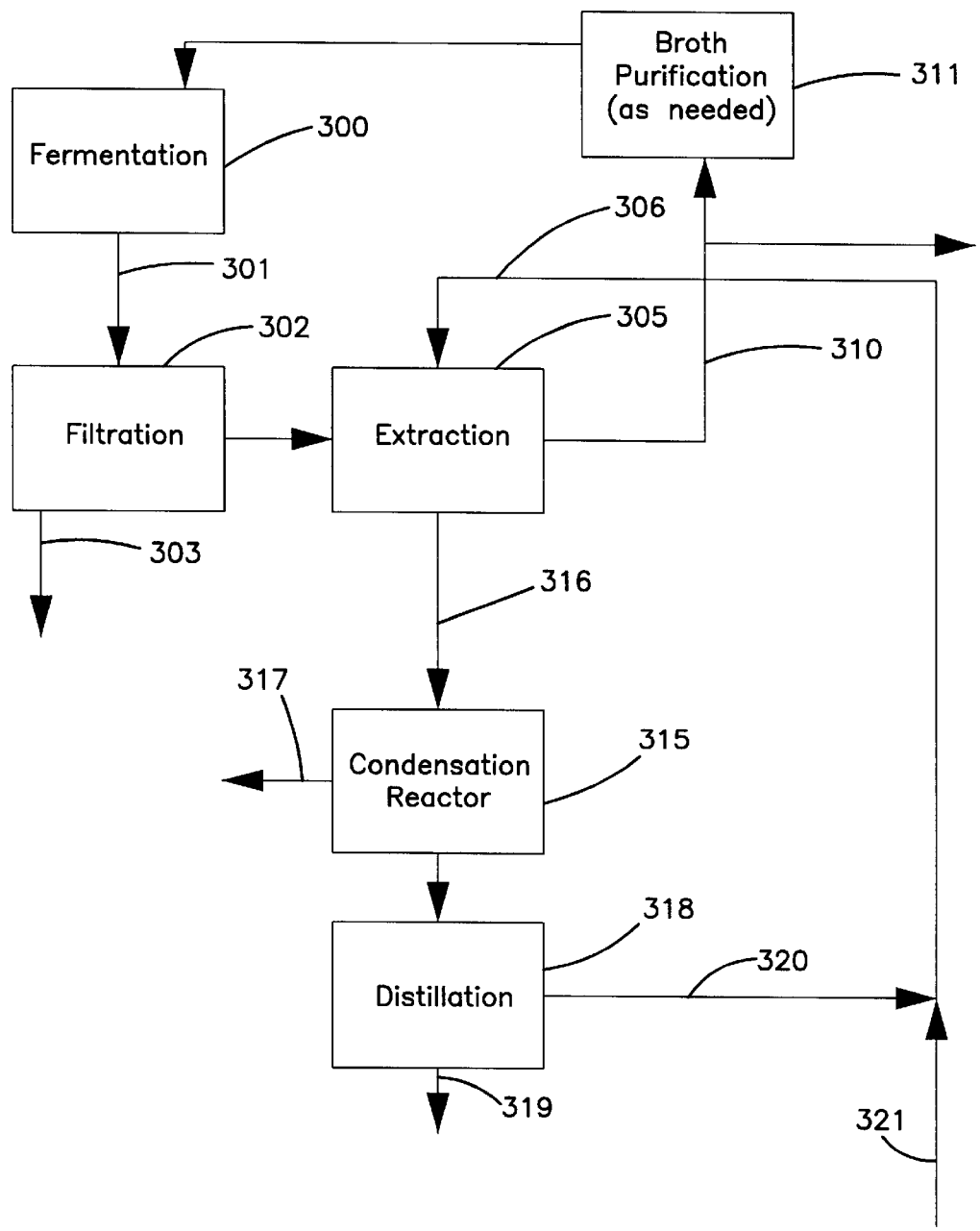
FIG. 10 is an alternate process flow diagram to the ones shown in FIGS. 1–9.

J. FIG. 10; Extraction of Lactic Acid; Formation of Alkyl Lactate Ester; Purification of Lactate Ester by Distillation.

Attention is now directed to FIG. 10. In FIG. 10 a fermentor is shown at 300. Fermentation broth is shown removed from the fermentor 300 at 301, and is directed through filter unit 302. Solids are removed via line 303. The aqueous solution from the filtration unit, or other source (modified or not) containing lactic acid and lactate, is shown directed into an extractor 305. The extractant is fed in via line 306, with the resulting aqueous raffinate, containing lactate salt therein, shown directed via line 310 into a purification unit 311, if desired, and then recycled as needed into fermentor 300. The extractant, containing the lactic acid, is shown directed a condensation reactor 315 via line 316. From the condensation reactor 315 water is drawn off via line 317. The product is then shown directed into distillation 318 for distillation resulting in separation of solvent from residual lactate product. If the selected extracting solvent contained an appropriate alcohol, the product within the distillation unit 318 will comprise an alkylactate ester. For example, the extracting solvent could contain ethanol, which readily forms esters with lactic acid. The alkyl lactate ester is purified in the distillation unit 318 and removed via line 319. The extracting solvent exits the distillation system via line 320 for possible recycle back to the extraction unit 305. Alcohol reacted in the condensation reactor 315 can be replaced via addition at line 321.

IX. Some Usable Process Schemes; Conditions

In this section some hypothetical process descriptions are provided, to indicate how the techniques described above can be applied.

A. Direct Distillation of Lactic Acid from Extractant

A strain of bacteria would be used to ferment dextrose to lactic acid at 45° C. in a batch mode. The fermentation medium would include dextrose, corn steep water, and other salts for efficient productivity of lactic acid. At the end of the batch, the final pH would be 3.9 with a lactate material concentration (lactic acid+dissociated salt) of 80 g per 1 of broth. This gives about 38 g/liter of undissociated lactic acid in broth. Preferably a bacteria which produces L-lactate at a chiral purity of at least 90% is used. The broth would be filtered to remove cell mass and other insolubles and contacted with an extracting solvent in a series of mixer settlers at 20° C. to 30° C. The extracting solvent would be 50 wt % Alamine 336, 40% dodecanol, and 10% IsoPar K. IsoParK is a mixture of alkanes. The aqueous to extract phase weight ratio would be 1:2. The extract and aqueous raffinate would be settled and carefully separated to avoid entrainment. The raffinate would be sent to a hold tank to be used for pH control on the next batch.

The extract would be sent to a falling film evaporator at 10 mm Hg pressure and 175° C. Lactic acid would be evaporated and then condensed to obtain a concentrated lactic acid solution with a small amount of residual solvent. The liquid lactic acid stream would be sent to a distillation column with a forced circulation reboiler with a bottoms at 150° C. and 200 mm Hg pressure to remove water. The average molecular weight of the oligomer exiting this distillation column would be about 500 g per mole. FASCAT 9102 catalyst would be added to the oligomer stream and the mixture recirculated through a falling film evaporator at 190° C. and 10 mm Hg pressure. A crude lactide stream would be obtained from the vapor phase of the falling film evaporator. About 5% of the material would be purged from the lactide reactor as lactic acid oligomers with an average molecular weight greater than 1,500 g per mole.

B. Aqueous Back Extract, Removal of Water to Make Prepolymer, then Lactide

A strain of bacteria would be used to ferment dextrose to lactic acid at 45° C. in a batch mode. The fermentation medium would include dextrose, corn steep water, and other salts for efficient productivity of lactic acid. At the end of the batch, the final pH is 3.9 with a lactate material concentration of 80 g per 1 of broth. This gives about 38 g/l of undissociated lactic acid in the broth. Preferably a bacteria which produces L-lactic acid with a chiral purity of at least 90% is used. The broth would be filtered to remove cell mass and other insolubles and contacted with an extracting solvent in a rotary disk contactor at 20° C. to 40° C. Tributyl phosphate would be the extracting solvent, and the aqueous to extract ratio would be 1:3. The extract is back extracted into water in a packed bed extraction column at 80° C. to 100° C. The column would be pressurized to 15 psig by nitrogen. The aqueous to extract ratio in the back extraction would be 1:2. The resulting aqueous phase would be about 19 wt % lactic acid. This aqueous stream would be sent to a triple effect evaporation system which removes water such that the lactic acid concentration increases to greater than 88 wt %, more preferably to greater than 92 wt %, and most preferably to greater than 95 wt %. At this point, lactic acid oligomers will have been formed and lactide can be made from this stream as described above.

C. Crystallization of Calcium Lactate with Recovery of Lactic Acid

A strain of bacteria would be is used to ferment dextrose to lactic acid at 48° C. in a two stage continuous fermentation providing 1000 kg per hour fermentation broth. The fermentation medium would have dextrose, corn steep water, and other salts for efficient productivity of lactic acid. The fermentation broth would have a pH of 3.86 and a total lactate anion concentration of lactate material of 90 grams per kilogram of broth. This would give about 45 g/kg of free lactic acid in the broth, and 55 g/kg calcium lactate. Preferably a system providing L-lactic acid at a chiral purity of at least 90% is used. The broth would be filtered to remove cell mass and other insolubles.

The clarified broth would be sent to an evaporator which runs at atmospheric pressure. Approximately 700 kg/hr water is distilled from the broth. The broth would be cooled in a forced-circulation cooling crystallizer that crystallizes the calcium lactate out of solution at 25° C. Ethanol would be added to the crystallizer at a rate of 85.1 kg/hr to decrease the solubility of the calcium lactate to 3.0 wt % calcium lactate. Solid calcium lactate would be recovered via filtration at a rate of 44.8 kg/hr, with 10.2 kg/hr calcium lactate remaining in the mother liquors. The solid salt would be recycled back to the fermentor for pH control with calcium carbonate being added as needed.

The salt-depleted broth would be contacted with an 350 kg/hr extracting solvent consisting of 20 wt % kerosene and 80% trioctylamine in a series of centrifugal contactors. The lactic acid and ethanol will distribute between the two liquid phases such that the organic layer contains about 10 wt % lactic acid and about 5 wt % ethanol. The aqueous stream would have ethanol, residual lactic acid, calcium lactate, and other broth components. The ethanol in this stream could be recovered via distillation or other technology for recycle, while the remaining aqueous stream would go to animal feed or other system. This aqueous stream with ethanol could be appropriate feed to a larger ethanol plant.

The extract with lactic acid and ethanol could be processed in a variety of ways to make needed lactic acid products. The stream could be subject to conditions to make ethyl lactate, which would then be distilled away from the remaining extracting solvent. The lactic acid could be back extracted into ethanol at an elevated temperature, and ethyl lactate could be made in the back extraction phase. Ethyl lactate made by these methods could be sold or used to make lactide. Of course, the ethanol could be separated from the lactic acid/extracting solvent phase and lactic acid could be processed by any of the methods described in this application to make lactic acid products that could be sold or used in the manufacture of PLA.

D. Direct Condensation in the Extractant Phase.

A strain of bacteria is used to ferment dextrose to lactic acid at 40° C. in a batch mode using calcium carbonate as a neutralization agent. At the end of the batch the final pH value is about 5.7 with a total lactate material concentration of 120 g/liter. The broth is filtered to remove cell mass and other insolubles. The free lactic acid concentration is less than 2 g/liter so a strong acid, either sulfuric acid or phosphoric acid, is added to decrease the pH value to about 2.0. The free lactic acid concentration is now about 118 g/liter. Calcium sulfate or calcium phosphate will be formed and crystallized out of solution. The solution will be filtered to remove the calcium salt.

The clarified and acidulated fermentation broth is contacted in a counter current fashion with Alamine 336 in a series of centrifugal contactors at about 40° C. The Alamine 336 can be predistilled at conditions similar to lactide formation conditions if needed to remove any impurities that may be volatile. The aqueous to organic phase ratio is 3:1 and the lactic acid concentration in the extractant phase is 21 wt % and is a single phase. The aqueous raffinate can be recycled to the extraction if needed.

The extractant phase is then taken to an evaporator at atmospheric pressure and 130° C. where water is evaporated. A second evaporator at 50 mm Hg and 160° C. also evaporates water and drives the condensation of lactic acid to lactic acid oligomers. The average molecular weight of the oligomers at this point is about 600 to 800. After this stage, the reaction mixture is cooled to about 60° C. where the mixture spontaneously splits into two phases; a nearly pure Alamine 336 phase and lactic acid oligomer- Alamine 336 phase. These phases are physically separated using a typical settler and the nearly pure Alamine 336 phase is recycled back to the extractor.

The tin (II) octanoate is added to the lactic acid oligomer-Alamine 336 phase at about 0.1 to 0.5 wt % of tin. The mixture is recirculated through a wiped film evaporator at about 180° C. and 5 mm Hg pressure. A crude lactide stream is obtained in the vapor phase.

A purge is taken from the evaporated recirculation loop and is processed to separate tin, possibly via ion exchange. The lactic acid oligomer- Alamine 336 is recycled or can be separated into a lactic acid oligomer rich stream and Alamine 336 rich stream via acid or base displacement as shown in Example 18 and 19. These two streams can then be recycled back into the process.

X. Experimental

Example 1

600 ml of caustic washed Alamine 336, 800 ml of 15 wt % aqueous lactic acid solution, and 100 ml of 50 wt % aqueous lactic acid solution were added to a separation funnel and mixed at room temperature. The phases were allowed to settle overnight. The phases were split and the top organic phase was centrifuged to remove entrained aqueous phase. The lactic acid concentration in the organic phase was determined to be 19.75 wt % by titration with a sodium hydroxide solution with phenolphthalein as an indicator. 304.6 grams of the Alamine 336 and lactic acid solution were added to a round bottom, 4-neck flask with a stir shaft, thermocouple, condenser, heating mantle and nitrogen purge. The solution was heated up to 200° C. and atmospheric pressure over 45 minutes. It was then allowed to cool to about 64° C. Then it was heated to 200° C. at 60 mm Hg pressure over 30 minutes. The flask was held at 200° C. and 70 mm Hg pressure for 45 minutes. The flask was cooled and the bottoms split into two phases upon cooling. The top phase was determined to be virtually all Alamine 336 by gas chromatography. The bottom phase was viscous and consisted of lactic acid oligomers and small amount of Alamine 336.

185.9 grams of Alamine 336 and lactic acid oligomer solution (about 54.8 wt % oligomer at average M.W. of 476) were added to a 500 ml round bottom, 4-neck flask with a stir shaft, high vacuum system, nitrogen purge, condenser, thermocouple, and heating mantle. With the solution at 125° C., 900 µl of FASCAT 9102, a butyltin tris-2-ethylhexanoate catalyst from Atochem was added. The solution was heated to 200° C. over four hours, and the mixture was held at 200° C. for 60 minutes. The pressure was held constant at about 1 mm Hg over the entire heating time. The condenser media temperature was held at 110° C. The overhead material crystallized upon cooling. The flask bottoms after heating were determined by gas chromatography to be virtually all Alamine 336. 139 g of material went overhead with virtually all the oligomer being transformed to lactide and distilled overhead. Some Alamine 336 also was distilled overhead due to the high temperature and low pressure. The presence of significant amounts of lactide in the distilled material was confirmed by gas chromatography. The lactide obtained had a chiral purity of less than 80%. The chiral purity can be improved by using lower temperatures and using high surface area equipment for the lactide reactor to allow for good mass transfer of lactide out of the reactor.

This example shows how the extracting solvent can be used as a solvent for the lactic acid oligomer and lactide formation.

Example 2

300 ml of Alamine 336 and 200 ml of a 22 wt % aqueous lactic acid solution was added to a separation funnel. The mixture was shaken and allowed to settle. Three liquid phases were obtained, which is typical for pure Alamine 336 extractions at these conditions. The lower aqueous phase was discarded. The top two organic phases were contacted with 100 ml of a 22 wt % aqueous lactic acid solution. The mixture was shaken and allowed to settle overnight. Only two phases were obtained, and the bottom aqueous phase was discarded. The top organic phase was centrifuged to remove any entrained water. The lactic acid concentration in the organic phase was 19.4 wt % as determined by titration. The water content in solution was 4.6 wt % as determined by titration using an automatic Karl Fischer titrator.

143.0 g of this Alamine 336 and lactic acid solution were added to a 500 ml, round bottom, 3-neck flask with thermocouple, vacuum, nitrogen purge, condenser, and stir shaft. The pressure was set at 20 mm Hg and the solution was heated from room temperature to 210° C. Fraction 1 was taken from the vapor phase with pot temperature between room temperature and 103° C. Fraction 2 was taken with the pot temperature between 103° C. and 150° C. Fraction 3 was taken with the pot temperature between 150° C. and 169° C. Fraction 4 was taken with the pot temperature between 169° C. and 210° C. The acid concentration in Fractions 1, 2, 3 and 4 were determined by titration to be 0.23 wt %, 16.1 wt %. 73.2 wt %, and 60.8 wt % respectively. The pot bottoms weighed 109.1 g and were two liquid phases at room temperature showing that some condensation occurred during the distillation. Fraction 4 was found to be about 2% lactide showing additional evidence for condensation. The addition of 23.8 g octanol caused the two bottom phases to become miscible. The single phase bottoms were titrated to find only 2.2 wt % lactic acid when corrected for the octanol. About 60% of the lactic acid was recovered overhead.

This example shows that distillation of the lactic acid from a less volatile extracting solvent is a viable process option.

Example 3

200 ml of dimethyl sulfoxide (DMSO) and 200 ml of a previously made Alamine 336 and lactic acid solution with 18.4 wt % lactic acid were added to a 500 ml round bottom, 3-neck flask with a stir shaft, temperature control, condenser, and heating mantle. The mixture was stirred and heated to 140° C. and held at 140° C. for 15 minutes. The two phases settled quickly, were separated, and were allowed to cool to room temperature. Samples of the bottom DMSO phase showed 11.3 wt % lactic acid by titration and 0.58 wt % Alamine 336 by gas chromatography. 40 ml of IsoPar K from Exxon was added to the DMSO phase in a separation funnel. The funnel was shaken at room temperature, and the phases were allowed to settle and were separated. Samples of the bottom DMSO phase showed 11.4 wt % lactic acid, 2.7 wt % water by Karl Fischer titration, and 0.05 wt % Alamine 336.

230.0 g of this DMSO and lactic acid solution was then placed in a 500 ml round bottom, 4-neck flask with stir shaft, vacuum, condenser, thermocouple, and heating mantle. The material was heated at atmospheric pressure to 180° C., collecting 42.0 g overhead. The material was allowed to cool. The acid concentration in the bottom phase was determined to be 12.4 wt %, showing some condensation by loss of acidity assuming no lactic acid evaporated. The material was then heated from room temperature to 117° C. with about a 60 mm Hg pressure over 60 minutes. Another 34.7 g of material was distilled overhead. This completed the lactic acid oligomer formation step.

146.7 g of DMSO and lactic acid oligomer solution remained for the lactide formation portion. 1.53 g of FAS-CAT 9102, a butyltin tris-2-ethylhexanoate catalyst, was added. A dry ice cold trap and nitrogen purge was added and the condenser was changed to an ethylene glycol media at 110° C. The mixture was heated from room temperature to 145° C. at 10 mm Hg pressure over 80 minutes. Only 7.8 g of material remained in the bottom of the flask. The receiver contained 116.2 g of material. The boiling point of DMSO is close enough to lactide that it was expected that a significant amount of DMSO would be distilled over. The presence of lactide in the overheads was confirmed by gas chromatography.

This example shows the feasibility of back extracting the lactic acid into a polar liquid from the extracting solvent, and using the polar liquid as a solvent to make lactic acid oligomer and lactide.

Example 4

Two solutions of lactic acid and Alamine 336 were made by contacting the Alamine 336 with various amounts and concentrations of aqueous lactic acid solutions. Alamine 336 mixtures with 4.35 wt % and 18.85 wt % lactic acid were obtained. 2 ml of the Alamine 336 and lactic acid solutions were contacted separately with the following solvents—dimethyl sulfoxide (DMSO); N,N-dimethyl foramide (DMF); 1,4-dioxane; N-methyl pyrrolidinone (NMP); and, 1,3-dioxalane. The samples were held at the specified temperature in an oil bath for about 45 to 60 minutes with regular mixing. The 1,4-dioxane and 1,3-dioxalane samples formed a single liquid phase at temperatures between 20° C. and about 80° C. A similar procedure was used for contacting Alamine 336 and lactic acid solutions with lactide and tetramethylene sulfone (TMSF). Phases were allowed to settle at specified temperature and then quickly separated by piping out the bottom phase. Samples were taken for titration with a sodium hydroxide solution with phenolphthalein as an indicator to determine lactic acid concentration, and gas chromatography to determine Alamine 336 concentrations. In all cases, the Alamine 336 phase was the least dense phase or the top phase.

Table 1 reports the lactic acid and Alamine 336 concentrations in the top and bottom phases. The partition coefficient is calculated by dividing the lactic acid concentration in the Alamine 336 top phase by the lactic acid concentration in the bottom polar liquid phase. The results show that significant amounts of lactic acid distributes into the polar liquid phase at these conditions. In some of the solvents, there was a significant amount of Alamine 336 co-extracted into the polar liquid phase. Dimethyl sulfoxide looks like a favorable solvent for this type of process because of the good selectivity for the lactic acid over the Alamine 336.

This example shows that lactic acid can be back extracted into a polar liquid from the initial extracting solvent with good efficiency. This example supports the feasibility of a process that uses a back extraction of the lactic acid into a second polar liquid.

TABLE 1

Results for back extraction of lactic acid into second polar phase

| Solvent | Sample | Temp ° C. | Lactic Acid Wt % | Alamine 336 Wt % | Partition Coefficient |
|---|---|---|---|---|---|
| DMSO | Top | 140 | 0.18 | 72.4 | 0.19 |
|  | Bottom |  | 0.93 | 0.0 |  |
|  | Top | 140 | 0.69 | 66.03 | 0.06 |
|  | Bottom |  | 11.78 | 0.98 |  |
| DMF | Top | 110 | 0.16 | 61.09 | 0.14 |
|  | Bottom |  | 1.13 | 1.17 |  |
|  | Top | 110 | 1.49 | 70.17 | 0.13 |
|  | Bottom |  | 11.36 | 19.23 |  |
| NMP | Top | 90 | 0.33 | 65.26 | 0.29 |
|  | Bottom |  | 1.13 | 1.72 |  |
|  | Top | 110 | 2.73 | 67.14 | 0.22 |
|  | Bottom |  | 12.2 | 19.71 |  |
| TMSF | Top | 140 | 0.88 | 71.69 | 0.21 |
|  | Bottom |  | 4.15 | 5.28 |  |
|  | Top | 140 | 1.25 | 73.06 | 0.17 |
|  | Bottom |  | 7.52 | 10.09 |  |
|  | Top | 140 | 1.50 | 78.10 | 0.17 |
|  | Bottom |  | 8.66 | 13.56 |  |
| Lactide | Top | 140 | 2.44 | n.d. | 0.82 |
|  | Bottom |  | 2.98[2] |  |  |

[2]calculated from overall mass balance
n.d. = not determined

Example 5

Alamine 336 and an aqueous lactic acid solution were contacted to obtain a 26.74 wt % lactic acid in the Alamine 336 phase. Ten grams of the lactic acid loaded Alamine 336 phase was contacted with 5 grams of triethylamine in a 125 ml separation funnel. The flask was shaken for one minute at 24° C., and the phases were allowed to settle. The top phase contained Alamine 336 excess triethylamine, and virtually no lactic acid while the bottom phase contained 43 wt % lactic acid and triethylamine. Acid concentrations were determined by titration with sodium hydroxide.

The back extraction was scaled up to allow the distillation experiment. Thirty grams of a 43 wt % lactic acid in triethylamine mixture was added to a 500 ml round bottom, 3-neck flask equipped with a dry ice trap, pressure gauge, condenser, thermocouple, and heating mantle. The triethylamine evaporated initially at 23° C. and 10 mm Hg. The temperature increased to 120° C. and the mixture was held at that temperature for 90 minutes. About 69% of the triethylamine evaporated out. The chiral purity of the lactic acid was not changed significantly after heating.

The triethylamine removal can be dramatically increased in the presence of a solvent. A 21.5 wt % lactic acid solution in a mixture of triethylamine and N-methyl-2-pyrrolidinone was heated at 55° C. and 10 mm Hg pressure for two hours and 48% of the triethylamine was evaporated from the solution. The remaining mixture was heated to 110° C. where it was held for 80 minutes. At this point, 96% of the triethylamine was evaporated. The chiral purity of the material was not significantly changed.

This example shows the back extraction of the lactic acid from the extracting solvent and then the ability to evaporate the back extraction solvent to obtain a concentrated lactic acid product.

Example 6

An excess of calcium lactate pentahydrate crystals were mixed for 2 hours at 30° C. with a solution containing 9% lactic acid and no ethanol. The resulting aqueous solution was analyzed for calcium ions to determine the concentration of the dissolved calcium lactate. It was found to be 7.49% calcium lactate.

An excess of calcium lactate pentahydrate crystals were mixed for 2 hours at 30° C. with a solution containing 11.26% lactic acid and 10% ethanol. The resulting aqueous solution was analyzed for calcium ions to determine the concentration of the dissolved calcium lactate. It was found to be 5.13% calcium lactate.

An excess of calcium lactate pentahydrate crystals were mixed for 2 hours at 30° C. with a solution containing 18.94% lactic acid and 24.8% ethanol. The resulting aqueous solution was analyzed for calcium ions to determine the concentration of the dissolved calcium lactate. It was found to be 2.99% calcium lactate.

These solubility measurements show the decrease in calcium lactate concentration as the amount of ethanol in solution increases. In a process, the addition of ethanol to the broth provide an additional driving force for the crystallization of calcium lactate from the broth.

Example 7

An aqueous feed solution containing 25% sodium lactate and 2.9 mol/Kg lactic acid was counter-currently extracted with hexanol at 80° C. The aqueous to organic phase ratio was 1:2.3 w/w and the number of stages was 5. The concentrations of lactic acid in the extract and in the raffinate were 1.0 mol/Kg and 0.2 mol/Kg respectively. The extract was back-extracted counter-currently with water at 30° C. The aqueous to organic phase ratio was 1:1.6 w/w and the number of stages was 6. The concentration of lactic acid in the regenerated extractant was less than 0.1 mol/Kg and that was in the resulting aqueous product solution was about 1.6 mol/kg.

This example shows the efficient recovery of lactic acid from a lactic acid and lactate salt stream using extraction and back extraction into water with an alcohol solvent.

Example 8

An aqueous feed solution containing 25% sodium lactate and 3.0 mol/Kg lactic acid was counter-currently extracted with TBP at 30° C. The aqueous to organic phase ratio was 1:2.3 w/w and the number of stages was 5. The concentrations of lactic acid in the extract and in the raffinate were 1.3 mol/Kg and 0.2 mol/Kg respectively. The extract was back-extracted counter-currently with water at 85° C. The aqueous to organic phase ratio was 1:1.7 w/w and the number of stages was 6. The concentration of lactic acid in the regenerated extractant was about 0.03 mol/Kg and that was in the resulting aqueous product solution was about 2.1 mol/kg.

This example shows the efficient recovery of lactic acid from a lactic acid and lactate salt stream using extraction and back extraction into water with an oxygenated phosphorus compound.

Example 9

An aqueous feed solution containing 0.5 mol/Kg lactic acid and 0.5 mol/kg sodium lactate was counter-currently extracted with Alamine 336 at 25° C. The aqueous to organic phase ratio was 5.6:1 w/w and the number of stages was 4. The concentrations of lactic acid in the extract and in the raffinate were 2.3 mol/Kg and 0.1 mol/Kg respectively. The extract was back-extracted counter-currently with water at 160° C. The aqueous to organic phase ratio was 1:1.2 w/w and the number of stages was 4. The concentration of lactic acid in the regenerated extractant was about 0.1 mol/Kg and that in the resulting aqueous product solution was about 2.7 mol/kg.

This sample shows the efficient recovery of lactic acid from a lactic acid and lactate salt stream using extraction and back extraction into water with a trialkylamine. Compared to the initial solution, the aqueous back extraction product has a higher lactic acid concentration.

Example 10

An aqueous feed solution containing 4 mol/Kg lactic acid was counter-currently extracted with hexanol at 80° C. The aqueous to organic phase ratio was 1:2.3 w/w and the number of stages was 6. The concentrations of lactic acid in the extract and in the raffinate were 1.8 mol/Kg and 0.2 mol/Kg respectively. The extract was back-extracted counter-currently with water at 30° C. The aqueous to organic phase ratio was 1:1.5 w/w and the number of stages was 7. The concentration of lactic acid in the regenerated extractant was less than 0.1 mol/Kg and that was in the resulting aqueous product solution was about 2.7 mol/kg.

This example shows the recovery of lactic acid from an aqueous solution with an alcohol solvent.

Example 11

An aqueous feed solution containing 4.5 mol/Kg lactic acid was counter-currently extracted with tri-butyl-phosphate (TBP) at 25° C. The aqueous to organic phase ratio was 1:2.3 w/w and the number of stages was 6. The concentrations of lactic acid in the extract and in the raffinate were 2.0 mol/Kg and 0.2 mol/Kg respectively. The extract was back-extracted counter-currently with water at 85° C. The aqueous to organic phase ratio was 1:1.7 w/w and the number of stages was 8. The concentration of lactic acid in the regenerated extractant was about 0.03 mol/Kg and that in the resulting aqueous product solution was about 3.5 mol/kg.

This example shows the recovery of lactic acid from an aqueous solution with an oxygenated phosphorus compound.

Example 12

An aqueous feed solution containing 0.5 mol/Kg lactic acid was counter-currently extracted with Alamine 336 at 25° C. The aqueous to organic phase ratio is 5.6:1 w/w and the number of stages was 4. The concentrations of lactic acid in the extract and in the raffinate were 2.3 mol/Kg and 0.1 mol/Kg respectively. The extract was back-extracted counter-currently with water at 160° C. The aqueous to organic phase ratio was 1:1.2 w/w and the number of stages was 4. The concentration of lactic acid in the regenerated extractant was about 0.1 mol/Kg and that in the resulting aqueous product solution was about 2.7 mol/kg.

This example shows the efficient recovery of lactic acid from an aqueous solution using a trialkylamine. Compared to the initial solution, the aqueous back extraction product has a higher lactic acid concentration.

Example 13

An aqueous feed solution containing 2 mol/Kg lactic acid was extracted by Alamine 336 at 25° C. in a single stage. The aqueous to organic phase ratio was 1:1 w/w. Three phases were formed; one bottom aqueous phase, and two organic phases. The concentrations of lactic acid in the combined organic extract and in the raffinate were 2.3 mol/Kg and 0.4 mol/Kg respectively. The combined organic extract was back-extracted counter-currently with water at 160° C. The aqueous to organic phase ratio was 1:1.2 w/w and the number of stages was 4. The concentration of lactic acid in the regenerated extractant was about 0.1 mol/Kg and that in the resulting aqueous product solution was about 2.7 mol/kg.

This example shows that a significant amount of lactic acid can be extracted in a single stage using a trialkylamine solvent. This system takes advantage of the three phase system that is formed when an extracting solvent has a high amount of Alamine 336 and other nonpolar compounds, like kerosene, and a minimal amount of oxygenated solvents, like hexanol or methylisobutylketone.

Example 14

An organic phase containing 3.13 mol lactic/Kg in Alamine 336 was added to a beaker. The beaker was heated on a hot plate to 150–160° C. and atmospheric pressure and maintained at those conditions for 7 hours. A sample of the contents was titrated with a 1.0N sodium hydroxide and found to contain 0.639 mol acid/Kg. The drop in acid concentration in the organic phase is a result of converting lactic acid molecules to lactic acid oligomers. The efficiency of conversion from lactic acid to the oligomer form was 79%.

This example shows the ability to make lactic acid oligomers at atmospheric pressure in a trialkylamine solvent.

Example 15

17.7 g of a solution containing 1.92 mol/Kg Alamine 336, 1.98 mol/kg Lactic acid and a drop of an antioxidant, was heated in a beaker, situated in an oil bath, to about 135–150° C. and kept at that temperature for 42 hours. Nitrogen was bubbled through the solution during the heating period. The beaker was connected to a distillation column, which was connected to a trap filled with water. At the end of the experiment, while still at elevated temperature there was only one phase in the beaker. After cooling, two organic phases were observed; 1.59 gram of a viscous bottom phase and 11.4 gram of a top phase. The amine and the proton concentrations in the bottom phase were determined by titration with a 0.1N hydrochloric acid solution and 0.1N sodium hydroxide solution, respectively. It contained 1 mol/kg amine and 0.957 mol/kg protons. As the heavy organic phase contains only the amine and a lactic acid oligomer, those figures allow calculating the molecular weight of the oligomer. It was found to be about 635, equivalent to that of an oligomer consisting of 8 lactic acid monomers. IR spectra support the conclusions based on this calculation. The concentration of the amine and protons were determined in the top phase to be 2.54 mol/kg and 0.02 mol/kg, respectively.

This example shows that the extracted lactic acid can be converted into lactic acid oligomer while in the extractant. Also, it shows the ability of the Alamine 336 and lactic acid oligomer system to spontaneously phase split upon cooling of the reaction mixture. The analysis of these phases shows the significantly larger top phase to be virtually all Alamine 336 and the smaller bottom phase to be the oligomer product and Alamine 336.

Example 16

An organic phase, containing 1.63 mol lactic acid in Alamine-336, was prepared. It was heated on a hot plate, in an open glass vessel, to 140–150° C. and kept at that temperature for 6 hours. Then, one drop Tin 2-Ethylhexanoate was added, the solution was heated to 180° C. and kept at that temperature for 3.5 hours. Part of the vapors distilled out during the heating was condensed on a cold glass (held above the heated vessel). The condensate was washed off the glass with chloroform and the NMR spectrum of the chloroform solution was taken. The NMR spectrum confirmed that the chloroform contained lactide as the main lactic acid product in the chloroform.

One drop Tin 2-Ethylhexanoate catalyst was added to a solution containing 1.02 mol/kg lactic acid oligomer of DP4–5 in Alamine-336. This mixture was heated on a hot plate, while in a beaker connected to a trap, to 170–190° C. and kept at that temperature for 5 hours. The condensate was washed out of the trap with chloroform and the IR spectrum of the chloroform solution was taken. Based on these spectra, one can conclude that the condensate collected in the trap contains a significant amount of lactide.

These two examples show that lactide can be made from lactic acid in the presence of a trialkylamine. In this case, the lactide production was at atmospheric pressure.

Example 17

16.2 g of octanol and 0.222 g of phosphoric acid were mixed for 15 minutes at 25° C. with 0.936 g solution containing 1.19 mmol Alamine 336 and 0.74 mmol lactic acid oligomer (DP8-9). After settling for 4 hours in a refrigerator, two phases were observed. Acid-base titrations show that 85% of the total amine was present in the light phase and a significant amount of the oligomer was present in the heavy phase.

16 g of isopropanol and 0.468 g of phosphoric acid were mixed for 15 minutes at 25° C. with 1.1 56 g solution containing 1.66 mmol Alamine 336 and 1.5 mmol lactic acid oligomer (DP8-9). After settling for 4 hours in a refrigerator, two phases were observed. Acid-base titrations show that 73% of the total amine was present in the light phase and a significant amount of the oligomer was present in the heavy phase.

3.06 of isopropanol and 0.324 g of acetic acid were mixed for 15 min at 25° C. with 0.733 g solution containing 1.04 mmol Alamine 336 and 0.57 mmol lactic acid oligomer (DP8-9). After settling for 4 hours in a refrigerator, two phases were observed. Acid-base titrations show that 82% of the total amine was present in the light phase and a significant amount of the oligomer was present in the heavy phase.

These three examples show that the addition of an alcohol solvent and either a relatively strong acid (phosphoric acid) or a weak acid (acetic acid) can separate trialkylamines from lactic acid oligomers via extraction or phase splitting.

Example 18

4.66 g of a solution containing 1.69 mol/kg lactic acid oligomer (DP-5) and 1.16 mol/kg Alamine 336 were mixed with 2.618 g hexane. Then 0.585 g of a concentrated ammonia solution was added (12.4 mmol ammonia). After mixing and settling, two phases were observed. The light phase was titrated by HCl and by NaOH to determine the concentrations of amine+ammonia and of protons (as lactic acid oligomer) respectively. 0.19 mmol prepolymer and 3.27 mmol amine+ammonia were found in said light phase. Based on the fact that ammonia solubility in hexane is negligible, the base concentration in the light phase represents separation about 60% of the oligomer from the amine in a single stage.

This example shows that the addition of a base such as ammonia can force the formation of a second phase and extract lactic acid oligomer from trialkylamine.

Example 19

1.79 g of a 8.7 mol/kg phosphoric acid solution was added to a mixture of 5.48 g of calcium lactate pentahydrate and 20.25 g of water. The solution was mixed for 2.5 hours at 85° C. A solid phase and an aqueous liquid phase were found. The solid phase was filtered, washed with water, and sampled. The solid was found to be virtually free of lactic material, and contain 80.2% and 77.0% of the total phosphate and calcium respectively. The remaining aqueous solution contains 77% on the lactate material in free acid form and 23% of the lactate material as a calcium lactate salt.

2.84 g of 8.7 mol/kg phosphoric acid solution, and 16.46 g butanol were added to a mixture of 7.83 g calcium lactate pentahydrate and 20.6 g water. The mixture was mixed for 30 minutes at 20° C. Three phases, a solid and two liquid, were found. The phases were separated, with the solid being washed with water. The solid was found to be virtually free of lactate material, and contained 68.7% and 72.3% of the total phosphate and calcium respectively. The bottom aqueous phase contained 66.9% of the lactate material, 31% of the total phosphate, and 26.7% of the total calcium. The organic phase contained 33% of the total lactate material. Thus a significant amount of lactate salt was simultaneously acidified and extracted into the organic phase.

These examples show the ability to acidulate with phosphoric acid and form calcium phosphate salt. The acidulated lactic acid can then be extracted with an appropriate solvent or isolated from the aqueous by other means.

Example 20

Fermentation broth with a final pH value of 3.87 and a total lactate material concentration of 79 g/liter as determined by high performance liquid chromatography was obtained. A number of different solvents were contacted with the broth to determine the lactic acid recovery in a single stage. The amount of free lactic acid in each phase was determined by titration with an aqueous sodium hydroxide solution. For the 100% Alamine 336 solvent, two organic phases were isolated and titrated and both values are reported. The partition coefficient is not reported for this system.

| Solvent Mixture | Lactic Acid Aqueous Phase wt % | Lactic Acid Organic Phase wt % | Partition Coefficient |
|---|---|---|---|
| 30 wt % TOPO 70 wt % MIBK | 2.24 | 2.36 | 1.05 |
| 82 wt % A336 10 wt % OctOH 8 wt % IPK | 1.52 | 5.09 | 3.35 |
| 100% A336 | 2.34 | 13.8 | N.A. 0.84 |
| 89 wt % A336 9 wt % DodecOH 2 wt % IPK | 4.76 | 1.84 | 2.6 |

Key
TOPO + trioctylphosphine oxide
MIBK = methyl isobutyl ketone
A336 = Alamine 336
OctOH = 1 octanol
IPK = IsoPar K
DodecOH = 1 dodecanol This example shows that a number of different extracting solvents give partition coefficient values that are suitable for industrial processes.

Example 21

Fermentation broth with a final pH of 3.87 and a total lactate material concentration of 79 g/liter as determined by high performance liquid chromatography was obtained. The broth was contacted three times with fresh extracting solvent consisting of 89 wt % Alamine 336, 9 wt % dodecanol, and 2 wt % IsoPar K with an aqueous to organic phase ratio of 3.0. The free lactic acid concentration was determined in each phase by titration with an aqueous sodium hydroxide solution.

| Stage | Lactic Acid Aqueous Phase wt % | Lactic Acid Organic Phase wt % | Partition Coefficient |
|---|---|---|---|
| 1 | 1.55 | 3.9 | 2.5 |
| 2 | 1.09 | 1.36 | 1.25 |
| 3 | 0.88 | 0.74 | 0.84 |

This example shows how the partition coefficient, which is a measure of extraction efficiency, decreases as more lactic acid is extracted from the broth, i.e. as the pH of the remaining broth increases.

What is claimed is:

1. A process for the production of lactic acid products from a mixture containing free lactic acid and dissolved lactate salt; said process comprising the steps of:

(a) providing an aqueous mixture of free lactic acid and dissolved lactate salt produced by, and separated from, acid tolerant lactate-producing microorganisms at an average incubation pH of no greater than 4.2 and wherein the aqueous mixture has a final incubation pH between 3.0 to 4.2 and includes a concentration of at least 50 g/liter of a free lactic acid enantiomer selected from free L-lactic acid and free D-lactic acid when separated from the acid tolerant lactate-producing microorganisms;

(b) preferentially separating free lactic acid from the aqueous mixture by selectively passing free lactic acid through a dense hydrophilic membrane into a second aqueous phase which includes a water miscible volatile amine weak base to provide a lactate salt of the volatile amine weak base, wherein the volatile amine weak base includes ammonia, trimethylamine, triethylamine or a mixture thereof; and (c) regenerating lactic acid from the lactate salt of the volatile amine weak base by selectively vaporizing the volatile amine weak base.

2. A process for the production of lactic acid products from a mixture containing free lactic acid and dissolved lactate salt; said process comprising the steps of:

(a) providing an aqueous mixture of free lactic acid and dissolved lactate salt produced by, and separated from, acid tolerant lactate-producing microorganisms, wherein the mixture is produced by the acid tolerant lactate-producing microorganisms at an average incubation pH of no greater than 4.2; and, the mixture has a final incubation pH of no greater than 4.2 when separated from the acid tolerant lactate-producing microorganisms;

(b) preferentially separating the free lactic acid and lactate salt in the mixture from one another to generate: a lactate salt containing stream; and, a lactic acid containing stream; wherein said step of preferentially separating includes selectively passing free lactic acid from the aqueous mixture through a dense hydrophilic membrane into a second aqueous phase which includes a water miscible volatile amine weak base to provide a lactate salt of the volatile amine weak base, wherein the volatile amine weak base includes ammonia, trimethylamine, triethylamine or a mixture thereof; and (c) regenerating lactic acid from the lactate salt of the volatile amine weak base by selectively vaporizing the volatile amine weak base.

3. A process according to claim 1 wherein:

(a) said step of providing a mixture comprises providing a mixture from a culture comprising acid tolerant lactate-producing microorganisms selected from lactate-producing bacteria, lactate-producing yeast and lactate-producing fungi.

4. A process according to claim 3 wherein:

(a) said step of providing a mixture comprises providing a mixture produced from a culture of acid tolerant recombinant microorganisms.

5. A process according to claim 3 wherein:

(a) said step of providing a mixture comprises providing a mixture produced from a culture of acid tolerant lactate-producing yeast.

6. A process according to claim 5 wherein:

(a) said step of providing a mixture comprises providing a mixture produced from a culture of acid tolerant lactate-producing recombinant yeast.

7. A process according to claim 5 wherein:

(a) said step of providing a mixture comprises providing a mixture having an average incubation pH, and a pH when separated from the culture, within the range of 3.0 to 4.0.

8. A process according to claim 3 wherein:

(a) said step of providing a mixture comprises providing a mixture produced from a culture of acid tolerant lactate-producing bacteria.

9. A process according to claim 3 wherein:

(a) said step of providing comprises providing an aqueous mixture of free lactic acid and dissolved lactate salt produced from a culture of acid tolerant lactate-producing microorganisms, wherein the aqueous mixture has a concentration of at least about 50 g/liter of a free lactic acid enantiomer selected from free L-lactic acid and free D-lactic acid.

10. A process according to claim 3 wherein:

(a) said step of providing comprises providing an aqueous mixture of free lactic acid and dissolved lactate salt produced from a culture of lactate-producing microorganisms wherein the mixture comprises L-lactic acid with a optical purity of at least 75% when produced by, and when separated from, the lactate-producing microorganisms.

11. A process according to claim 10 wherein:

(a) said step of providing comprises providing an aqueous mixture of free lactic acid and dissolved lactate salt produced from a culture of acid tolerant lactate-producing microorganisms with a production rate sufficient to provide the mixture when produced from, and when separated from, the lactate-producing microorganisms, with a concentration of L-lactic acid of at least 80 g/liter.

12. A process according to claim 3 wherein:

(a) said step of providing comprises providing an aqueous mixture of free lactic acid and dissolved lactate salt from a fermentation process comprising a culture of acid tolerant lactate-producing microorganisms to which lactate salt has been added.

13. A process according to claim 3 wherein:

(a) said step of preferentially separating is conducted following a step of modifying the mixture after it is separated from the lactate producing microorganisms.

14. A process for the production of lactic acid products from a mixture containing free lactic acid and dissolved lactate salt; said process comprising the steps of:

(a) providing an aqueous mixture of free lactic acid and dissolved lactate salt produced from and separated from a culture of acid tolerant lactate-producing microorganisms;

(i) the mixture being the result of production at an average incubation pH of no greater than 4.2; and, the mixture having a final incubation pH of no greater than 4.2 when separated from the culture; and, (ii) the mixture being separated from a culture acid tolerant lactate-producing microorganisms having a production rate sufficient to provide the mixture when produced from, and when separated from, the lactate-producing microooganisms at a concentration of at least 50 g/liter of a free lactic acid enantiomer selected from free L-lactic acid and free D-lactic acid; and (b) preferentially separating the lactic acid and lactate salt in the mixture from one another to generate;

(i) a lactate salt stream; and, (ii) a lactic acid containing stream.

15. A process according to claim 14 wherein:

(a) said step of providing a mixture comprises providing a mixture separated from a culture comprising acid tolerant lactate-producing bacteria.

16. A process according to claim 14 further including the step of:

(a) modifying the mixture by adding acid thereto following separation from the lactate-producing microorganisms and before said step of preferentially separating.

17. A process according to claim 14 wherein:

(a) said step of preferentially separating comprises a step of preferentially removing the lactate salt from the mixture.

18. A process according to claim 14 wherein:

(a) said process is conducted such that said isolated lactate salt stream is a stream selected from calcium lactate, sodium lactate, ammonium lactate and mixtures thereof.

19. A process according to claim 18 wherein:
(a) at least a portion of the separated lactate salt is added to a culture of acid tolerant lactate-producing microorganisms.

20. A process according to claim 14 wherein:
(a) said step of preferentially separating is selected from:
 (i) preferentially extracting lactic acid into a non-aqueous phase and condensing lactic acid in the non-aqueous phase to form oligomer; and,
 (ii) preferentially extracting lactic acid into a non-aqueous phase and separating the lactic acid from the non-aqueous phase by a step selected from:
  (A) distillation; and,
  (B) back extraction into another solvent.

* * * * *

UNITED STATES PATENT AND TRADEMARK OFFICE
CERTIFICATE OF CORRECTION

PATENT NO.        : 6,320,077 B1                                              Page 1 of 1
APPLICATION NO. : 09/132720
DATED              : November 20, 2001
INVENTOR(S)      : Eyal et al.

It is certified that error appears in the above-identified patent and that said Letters Patent is hereby corrected as shown below:

Title page (54) Title: "AND, PRODUCT" should read --AND, PRODUCTS--

Title page (75) Inventors: After "Kolstad, Wayzata, both of MN (US)" insert --Xiangsheng Meng, Chanhassen, MN (US)--

Signed and Sealed this

Twentieth Day of February, 2007

JON W. DUDAS
*Director of the United States Patent and Trademark Office*